(12) United States Patent
Jones et al.

(10) Patent No.: US 9,456,901 B2
(45) Date of Patent: *Oct. 4, 2016

(54) LASER-PRODUCED POROUS STRUCTURE

(75) Inventors: Eric Jones, Limerick (IE); Christopher J. Sutcliffe, Liverpool (GB); Robin Stamp, Manchester (GB)

(73) Assignees: Howmedica Osteonics Corp., Mahwah, NJ (US); The University Of Liverpool (GB)

( * ) Notice: Subject to any disclaimer, the term of this patent is extended or adjusted under 35 U.S.C. 154(b) by 787 days.

This patent is subject to a terminal disclaimer.

(21) Appl. No.: 12/846,327

(22) Filed: Jul. 29, 2010

(65) Prior Publication Data
US 2011/0014081 A1 Jan. 20, 2011

Related U.S. Application Data

(63) Continuation of application No. 11/027,421, filed on Dec. 30, 2004, now abandoned.

(51) Int. Cl.
*B22F 3/11* (2006.01)
*A61F 2/30* (2006.01)
(Continued)

(52) U.S. Cl.
CPC ....... *A61F 2/30907* (2013.01); *A61F 2/30771* (2013.01); *A61F 2/30965* (2013.01); *A61L 27/04* (2013.01); *A61L 27/56* (2013.01); *B22F 3/1055* (2013.01); *B22F 3/1109* (2013.01); *B23K 26/382* (2013.01); *B23K 26/40* (2013.01); *B23K 26/402* (2013.01); *C23C 4/02* (2013.01);
(Continued)

(58) Field of Classification Search
CPC ....................................................... B22F 3/21

USPC ............................................................ 419/2
See application file for complete search history.

(56) References Cited

U.S. PATENT DOCUMENTS 14,403 A 3/1856 Brown et al.
222,687 A 12/1879 Fresco
(Continued)

FOREIGN PATENT DOCUMENTS

CA 2295896 A1 7/2000
CN 101301230 A 11/2008
(Continued)

OTHER PUBLICATIONS

"Direct Generation of Metal Parts and Tools by Selective Laser Powder Remelting (SLPR)", W. Meiners, C. Over, K. Wissenbach, R. Poprawe, pp. 655-661.
(Continued)

*Primary Examiner* — Jessee Roe
*Assistant Examiner* — Christopher Kessler
(74) *Attorney, Agent, or Firm* — Lerner, David, Littenberg, Krumholz & Mentlik, LLP

(57) ABSTRACT

The present invention disclosed a method of producing a three-dimensional porous tissue in-growth structure. The method includes the steps of depositing a first layer of metal powder and scanning the first layer of metal powder with a laser beam to form a portion of a plurality of predetermined unit cells. Depositing at least one additional layer of metal powder onto a previous layer and repeating the step of scanning a laser beam for at least one of the additional layers in order to continuing forming the predetermined unit cells. The method further includes continuing the depositing and scanning steps to form a medical implant.

21 Claims, 32 Drawing Sheets

(51) Int. Cl.
*A61L 27/04* (2006.01)
*A61L 27/56* (2006.01)
*B22F 3/105* (2006.01)
*C23C 4/02* (2006.01)
*C23C 4/18* (2006.01)
*C23C 24/10* (2006.01)
*C23C 26/02* (2006.01)
*B23K 26/40* (2014.01)
*A61F 2/28* (2006.01)
*A61F 2/36* (2006.01)
*A61F 2/38* (2006.01)
*A61F 2/44* (2006.01)
*A61F 2/34* (2006.01)

(52) U.S. Cl.
CPC ............... *C23C4/18* (2013.01); *C23C 24/10* (2013.01); *C23C 26/02* (2013.01); *A61F 2/2803* (2013.01); *A61F 2/3094* (2013.01); *A61F 2/30767* (2013.01); *A61F 2/36* (2013.01); *A61F 2/3662* (2013.01); *A61F 2/389* (2013.01); *A61F 2/3859* (2013.01); *A61F 2/4455* (2013.01); *A61F 2002/30011* (2013.01); *A61F 2002/3092* (2013.01); *A61F 2002/3097* (2013.01); *A61F 2002/30113* (2013.01); *A61F 2002/30143* (2013.01); *A61F 2002/30146* (2013.01); *A61F 2002/30153* (2013.01); *A61F 2002/30154* (2013.01); *A61F 2002/30199* (2013.01); *A61F 2002/30243* (2013.01); *A61F 2002/30283* (2013.01); *A61F 2002/30329* (2013.01); *A61F 2002/30736* (2013.01); *A61F 2002/30785* (2013.01); *A61F 2002/30789* (2013.01); *A61F 2002/30879* (2013.01); *A61F 2002/30892* (2013.01); *A61F 2002/30904* (2013.01); *A61F 2002/30915* (2013.01); *A61F 2002/30925* (2013.01); *A61F 2002/30952* (2013.01); *A61F 2002/30962* (2013.01); *A61F 2002/30968* (2013.01); *A61F 2002/30971* (2013.01); *A61F 2002/3403* (2013.01); *A61F 2002/3411* (2013.01); *A61F 2002/3417* (2013.01); *A61F 2002/3425* (2013.01); *A61F 2002/3472* (2013.01); *A61F 2002/3474* (2013.01); *A61F 2002/4475* (2013.01); *A61F 2220/0025* (2013.01); *A61F 2230/0006* (2013.01); *A61F 2230/0017* (2013.01); *A61F 2230/0019* (2013.01); *A61F 2230/0021* (2013.01); *A61F 2230/0063* (2013.01); *A61F 2230/0071* (2013.01); *A61F 2250/0023* (2013.01); *A61F 2310/00017* (2013.01); *A61F 2310/00023* (2013.01); *A61F 2310/00029* (2013.01); *A61F 2310/00095* (2013.01); *A61F 2310/00131* (2013.01); *A61F 2310/00401* (2013.01); *A61F 2310/00407* (2013.01); *A61F 2310/00413* (2013.01); *A61F 2310/00491* (2013.01); *A61F 2310/00544* (2013.01); *B23K 2201/35* (2013.01); *B23K 2203/02* (2013.01); *B23K 2203/04* (2013.01); *B23K 2203/08* (2013.01); *B23K 2203/14* (2013.01); *B23K 2203/42* (2015.10); *B23K 2203/50* (2013.01); *B23K 2203/52* (2013.01); *Y02P 10/295* (2015.11)

(56) References Cited

U.S. PATENT DOCUMENTS

| | | |
|---|---|---|
| 2,373,769 A | 4/1945 | Macy |
| 3,520,099 A | 7/1970 | Mattes |
| 3,556,918 A | 1/1971 | Lemelson |
| 3,605,123 A | 9/1971 | Pratt et al. |
| 3,806,961 A | 4/1974 | Muller |
| 3,816,855 A | 6/1974 | Saleh |
| 3,826,054 A | 7/1974 | Culpepper, Jr. |
| 4,047,349 A | 9/1977 | Aguilar, Jr. |
| 4,085,466 A | 4/1978 | Goodfellow et al. |
| 4,117,302 A | 9/1978 | Earle et al. |
| 4,154,040 A | 5/1979 | Pace |
| 4,164,794 A | 8/1979 | Spector et al. |
| 4,202,055 A | 5/1980 | Reiner et al. |
| 4,218,494 A | 8/1980 | Belmondo et al. |
| 4,247,508 A | 1/1981 | Housholder |
| 4,305,340 A | 12/1981 | Iwaki et al. |
| 4,344,193 A | 8/1982 | Kenny |
| 4,385,404 A | 5/1983 | Sully et al. |
| 4,444,818 A | 4/1984 | Tominaga et al. |
| 4,474,861 A | 10/1984 | Ecer |
| 4,502,161 A | 3/1985 | Wall |
| 4,513,045 A | 4/1985 | Bondoc et al. |
| 4,543,158 A | 9/1985 | Bondoc et al. |
| 4,636,219 A | 1/1987 | Pratt et al. |
| 4,644,942 A | 2/1987 | Sump |
| 4,673,408 A | 6/1987 | Grobbelaar |
| 4,673,409 A | 6/1987 | Van Kampen |
| 4,714,473 A | 12/1987 | Bloebaum |
| 4,714,474 A | 12/1987 | Brooks, Jr. et al. |
| 4,719,908 A | 1/1988 | Averill et al. |
| 4,766,029 A | 8/1988 | Brock et al. |
| 4,863,538 A | 9/1989 | Deckard |
| 4,944,817 A | 7/1990 | Bourell et al. |
| 4,961,154 A | 10/1990 | Pomerantz et al. |
| 4,969,302 A | 11/1990 | Coggan et al. |
| 4,969,907 A | 11/1990 | Koch et al. |
| 4,990,163 A | 2/1991 | Ducheyne et al. |
| 5,002,572 A | 3/1991 | Picha |
| 5,004,476 A | 4/1991 | Cook |
| 5,017,753 A | 5/1991 | Deckard |
| 5,024,670 A | 6/1991 | Smith et al. |
| 5,031,120 A | 7/1991 | Pomerantz et al. |
| 5,034,186 A | 7/1991 | Shimamune et al. |
| 5,053,090 A | 10/1991 | Beaman et al. |
| 5,067,964 A | 11/1991 | Richmond et al. |
| 5,076,869 A | 12/1991 | Bourell et al. |
| 5,080,674 A | 1/1992 | Jacobs et al. |
| 5,090,174 A | 2/1992 | Fragale |
| 5,108,432 A | 4/1992 | Gustavson |
| 5,108,441 A | 4/1992 | McDowell |
| 5,147,402 A | 9/1992 | Bohler et al. |
| 5,150,304 A | 9/1992 | Berchem et al. |
| 5,155,324 A | 10/1992 | Deckard et al. |
| 5,158,574 A | 10/1992 | Stone |
| 5,171,282 A | 12/1992 | Pequignot |
| 5,176,710 A | 1/1993 | Hahn et al. |
| 5,192,328 A | 3/1993 | Winters |
| 5,219,362 A | 6/1993 | Tuke et al. |
| 5,274,565 A | 12/1993 | Reuben |
| 5,282,861 A | 2/1994 | Kaplan |
| 5,282,870 A | 2/1994 | Moser et al. |
| 5,287,435 A | 2/1994 | Cohen et al. |
| 5,314,478 A | 5/1994 | Oka et al. |
| 5,323,954 A | 6/1994 | Shetty et al. |
| 5,336,518 A | 8/1994 | Narayanan et al. |
| 5,352,405 A | 10/1994 | Beaman et al. |
| 5,356,433 A | 10/1994 | Rowland et al. |
| 5,358,529 A | 10/1994 | Davidson |
| 5,368,602 A | 11/1994 | de la Torre |
| 5,370,692 A | 12/1994 | Fink et al. |
| 5,386,500 A | 1/1995 | Pomerantz et al. |
| 5,398,193 A * | 3/1995 | deAngelis .................. 700/119 |
| 5,425,210 A | 6/1995 | Zafir |
| 5,443,510 A | 8/1995 | Shetty et al. |
| 5,443,518 A | 8/1995 | Insall |
| 5,461,839 A | 10/1995 | Beck |
| 5,486,599 A | 1/1996 | Saunders et al. |
| 5,490,962 A | 2/1996 | Cima et al. |
| 5,496,372 A | 3/1996 | Hamamoto et al. |
| 5,504,300 A | 4/1996 | Devanathan et al. |
| 5,507,815 A | 4/1996 | Wagner et al. |

(56) References Cited

U.S. PATENT DOCUMENTS

| | | |
|---|---|---|
| 5,510,066 A | 4/1996 | Fink et al. |
| 5,514,183 A | 5/1996 | Epstein et al. |
| 5,518,680 A | 5/1996 | Cima et al. |
| 5,526,627 A | 6/1996 | Beck |
| 5,549,700 A | 8/1996 | Graham et al. |
| 5,571,185 A | 11/1996 | Schug |
| 5,571,196 A | 11/1996 | Stein |
| 5,580,353 A | 12/1996 | Mendes et al. |
| 5,609,646 A | 3/1997 | Field et al. |
| 5,616,294 A | 4/1997 | Deckard |
| 5,624,463 A | 4/1997 | Stone et al. |
| 5,632,745 A | 5/1997 | Schwartz |
| 5,640,667 A | 6/1997 | Freitag et al. |
| 5,648,450 A | 7/1997 | Dickens, Jr. et al. |
| 5,665,118 A | 9/1997 | LaSalle et al. |
| 5,681,354 A | 10/1997 | Eckhoff |
| 5,702,448 A | 12/1997 | Buechel et al. |
| 5,714,103 A | 2/1998 | Bauer et al. |
| 5,716,358 A | 2/1998 | Ochoa et al. |
| 5,728,162 A | 3/1998 | Eckhoff |
| 5,729,946 A | 3/1998 | Beck |
| 5,735,903 A | 4/1998 | Li et al. |
| 5,749,874 A | 5/1998 | Schwartz |
| 5,768,134 A | 6/1998 | Swaelens et al. |
| 5,769,092 A | 6/1998 | Williamson, Jr. |
| 5,769,899 A | 6/1998 | Schwartz et al. |
| 5,773,789 A | 6/1998 | Devanathan et al. |
| 5,776,201 A | 7/1998 | Colleran et al. |
| 5,782,908 A | 7/1998 | Cahalan et al. |
| 5,795,353 A | 8/1998 | Felt |
| 5,798,924 A | 8/1998 | Eufinger et al. |
| 5,824,098 A | 10/1998 | Stein |
| 5,824,102 A | 10/1998 | Buscayret |
| 5,839,247 A | 11/1998 | Beck |
| 5,857,303 A | 1/1999 | Beck et al. |
| 5,866,113 A | 2/1999 | Hendriks et al. |
| 5,879,387 A | 3/1999 | Jones et al. |
| 5,879,398 A | 3/1999 | Swarts et al. |
| 5,928,285 A | 7/1999 | Bigliani et al. |
| 5,973,222 A | 10/1999 | Devanathan et al. |
| 5,987,838 A | 11/1999 | Beck |
| 5,989,472 A | 11/1999 | Ashby et al. |
| 6,013,855 A | 1/2000 | McPherson et al. |
| 6,042,774 A | 3/2000 | Wilkening et al. |
| 6,046,426 A | 4/2000 | Jeantette et al. |
| 6,049,054 A | 4/2000 | Panchison et al. |
| 6,087,553 A | 7/2000 | Cohen et al. |
| 6,096,043 A | 8/2000 | Techiera et al. |
| 6,112,109 A | 8/2000 | D'Urso |
| 6,128,866 A | 10/2000 | Wearne |
| 6,132,468 A | 10/2000 | Mansmann |
| 6,139,585 A | 10/2000 | Li |
| 6,149,689 A | 11/2000 | Grundei et al. |
| 6,164,032 A | 12/2000 | Beck |
| 6,171,340 B1 | 1/2001 | McDowell |
| 6,190,407 B1 | 2/2001 | Ogle et al. |
| 6,206,924 B1 | 3/2001 | Timm |
| 6,206,927 B1 | 3/2001 | Fell et al. |
| 6,209,621 B1 | 4/2001 | Treacy |
| 6,215,093 B1 | 4/2001 | Meiners et al. |
| 6,217,615 B1 | 4/2001 | Sioshansi et al. |
| 6,248,131 B1 | 6/2001 | Felt et al. |
| 6,251,143 B1 | 6/2001 | Schwartz et al. |
| 6,254,639 B1 | 7/2001 | Peckitt |
| 6,261,322 B1 | 7/2001 | Despres, III et al. |
| 6,261,493 B1 | 7/2001 | Gaylo et al. |
| 6,280,478 B1 | 8/2001 | Richter et al. |
| 6,283,997 B1 | 9/2001 | Garg et al. |
| 6,299,645 B1 | 10/2001 | Ogden |
| 6,344,061 B1 | 2/2002 | Leitao et al. |
| 6,355,086 B2 | 3/2002 | Brown et al. |
| 6,370,382 B1 | 4/2002 | Kang et al. |
| 6,371,958 B1 | 4/2002 | Overaker |
| 6,385,585 B1 | 5/2002 | Jonsson et al. |
| 6,395,327 B1 | 5/2002 | Shetty |
| 6,406,497 B2 | 6/2002 | Takei |
| 6,415,574 B2 | 7/2002 | Beck |
| 6,454,811 B1 | 9/2002 | Sherwood et al. |
| 6,476,343 B2 | 11/2002 | Keicher et al. |
| 6,482,209 B1 | 11/2002 | Engh et al. |
| 6,494,914 B2 | 12/2002 | Brown et al. |
| 6,497,728 B2 | 12/2002 | Yong |
| 6,520,996 B1 | 2/2003 | Manasas et al. |
| 6,530,951 B1 | 3/2003 | Bates et al. |
| 6,551,608 B2 | 4/2003 | Yao |
| 6,558,421 B1 | 5/2003 | Fell et al. |
| 6,582,715 B1 | 6/2003 | Barry et al. |
| 6,589,283 B1 | 7/2003 | Metzger et al. |
| 6,592,598 B2 | 7/2003 | Vibe-Hansen et al. |
| 6,599,301 B2 | 7/2003 | Vibe-Hansen et al. |
| 6,599,322 B1 | 7/2003 | Amrich et al. |
| 6,610,067 B2 | 8/2003 | Tallarida et al. |
| 6,626,945 B2 | 9/2003 | Simon et al. |
| 6,632,246 B1 | 10/2003 | Simon et al. |
| 6,652,246 B1 | 11/2003 | Lin et al. |
| 6,652,587 B2 | 11/2003 | Felt et al. |
| 6,676,892 B2 | 1/2004 | Das et al. |
| 6,679,917 B2 | 1/2004 | Ek |
| 6,682,567 B1 | 1/2004 | Schroeder |
| 6,686,437 B2 | 2/2004 | Buchman et al. |
| 6,699,252 B2 | 3/2004 | Farr, II et al. |
| 6,702,848 B1 | 3/2004 | Zilla et al. |
| 6,709,462 B2 | 3/2004 | Hanssen |
| 6,712,822 B2 | 3/2004 | Re et al. |
| 6,712,856 B1 | 3/2004 | Carignan et al. |
| 6,716,957 B2 | 4/2004 | Tunc |
| 6,743,232 B2 | 6/2004 | Overaker et al. |
| 6,770,099 B2 | 8/2004 | Andriacchi et al. |
| 6,802,864 B2 | 10/2004 | Tornier |
| 6,846,329 B2 | 1/2005 | McMinn |
| 6,850,125 B2 | 2/2005 | Norman et al. |
| 6,852,125 B2 | 2/2005 | Simon et al. |
| 6,855,165 B2 | 2/2005 | Fell et al. |
| 6,863,689 B2 | 3/2005 | Ralph et al. |
| 6,866,684 B2 | 3/2005 | Fell et al. |
| 6,893,463 B2 | 5/2005 | Fell et al. |
| 6,911,044 B2 | 6/2005 | Fell et al. |
| 6,916,341 B2 | 7/2005 | Rolston |
| 6,921,264 B2 | 7/2005 | Mayer et al. |
| 6,923,831 B2 | 8/2005 | Fell et al. |
| 6,932,610 B2 | 8/2005 | Ono et al. |
| 6,993,406 B1 | 1/2006 | Cesarano, III et al. |
| 7,051,417 B2 | 5/2006 | Michelson |
| 7,168,283 B2 | 1/2007 | Van Note et al. |
| 7,332,537 B2 | 2/2008 | Bredt et al. |
| 7,388,972 B2 | 6/2008 | Kitson |
| 7,494,507 B2 | 2/2009 | Dixon et al. |
| 7,497,876 B2 | 3/2009 | Tuke et al. |
| 7,521,017 B2 | 4/2009 | Kunze et al. |
| 7,632,575 B2 | 12/2009 | Justin et al. |
| 7,637,942 B2 | 12/2009 | Mangiardi et al. |
| 7,674,517 B2 | 3/2010 | Ramsey et al. |
| 7,718,109 B2 | 5/2010 | Robb et al. |
| 7,747,305 B2 | 6/2010 | Dean et al. |
| 7,779,890 B2 | 8/2010 | Frasier et al. |
| 7,875,083 B2 | 1/2011 | Sudmann |
| 8,029,575 B2 | 10/2011 | Borden |
| 8,090,540 B2 | 1/2012 | Leo et al. |
| 8,247,333 B2 | 8/2012 | Sypeck et al. |
| 8,308,807 B2 | 11/2012 | Seebeck et al. |
| 8,430,930 B2 | 4/2013 | Hunt |
| 8,551,173 B2 | 10/2013 | Lechmann et al. |
| 8,796,015 B2 | 8/2014 | Gingras |
| 8,843,229 B2 | 9/2014 | Vanasse et al. |
| 8,888,862 B2 | 11/2014 | McDonnell et al. |
| 8,983,646 B1 | 3/2015 | Hanna |
| 2001/0014403 A1 | 8/2001 | Brown et al. |
| 2002/0010512 A1 | 1/2002 | Takei |
| 2002/0015654 A1 | 2/2002 | Das et al. |
| 2002/0016635 A1 | 2/2002 | Despres et al. |
| 2002/0127328 A1 | 9/2002 | Shetty |
| 2002/0130112 A1 | 9/2002 | Manasas et al. |
| 2002/0151983 A1 | 10/2002 | Shetty |
| 2002/0173855 A1 | 11/2002 | Mansmann |

(56) References Cited

U.S. PATENT DOCUMENTS

| | | |
|---|---|---|
| 2002/0187458 A1 | 12/2002 | Dolabdjian et al. |
| 2002/0198528 A1 | 12/2002 | Engh et al. |
| 2003/0032351 A1 | 2/2003 | Horner et al. |
| 2003/0033018 A1 | 2/2003 | Merchant |
| 2003/0045941 A1 | 3/2003 | Lewallen |
| 2003/0055500 A1 | 3/2003 | Fell et al. |
| 2003/0055501 A1 | 3/2003 | Fell et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0060888 A1 | 3/2003 | Fell et al. |
| 2003/0069638 A1 | 4/2003 | Barlow et al. |
| 2003/0069718 A1 | 4/2003 | Hollister et al. |
| 2003/0153977 A1 | 8/2003 | Suguro et al. |
| 2003/0153981 A1 | 8/2003 | Wang et al. |
| 2003/0155686 A1 | 8/2003 | Hawkins et al. |
| 2003/0158606 A1 | 8/2003 | Coon et al. |
| 2003/0209305 A1 | 11/2003 | Smith et al. |
| 2003/0220696 A1 | 11/2003 | Levine et al. |
| 2004/0006393 A1 | 1/2004 | Burkinshaw |
| 2004/0009228 A1 | 1/2004 | Tormala et al. |
| 2004/0015170 A1 | 1/2004 | Tallarida et al. |
| 2004/0023586 A1 | 2/2004 | Tilton |
| 2004/0044414 A1 | 3/2004 | Nowakowski |
| 2004/0054416 A1 | 3/2004 | Wyss et al. |
| 2004/0059356 A1 | 3/2004 | Gingras |
| 2004/0098132 A1 | 5/2004 | Andriacchi et al. |
| 2004/0121110 A1 | 6/2004 | Schmidt et al. |
| 2004/0143339 A1 | 7/2004 | Axelson et al. |
| 2004/0148030 A1 | 7/2004 | Ek |
| 2004/0153163 A1 | 8/2004 | Posner |
| 2004/0162622 A1 | 8/2004 | Simon et al. |
| 2004/0167633 A1 | 8/2004 | Wen et al. |
| 2004/0191106 A1 | 9/2004 | O'Neill et al. |
| 2004/0199249 A1 | 10/2004 | Fell |
| 2004/0199250 A1 | 10/2004 | Fell |
| 2004/0204766 A1 | 10/2004 | Siebel |
| 2004/0230315 A1 | 11/2004 | Ek |
| 2004/0243237 A1 | 12/2004 | Unwin et al. |
| 2004/0267363 A1 | 12/2004 | Fell et al. |
| 2005/0033424 A1 | 2/2005 | Fell |
| 2005/0043816 A1 | 2/2005 | Datta et al. |
| 2005/0079200 A1 | 4/2005 | Rathenow et al. |
| 2005/0085918 A1 | 4/2005 | Soffiati et al. |
| 2005/0085922 A1 | 4/2005 | Shappley et al. |
| 2005/0100578 A1 | 5/2005 | Schmid et al. |
| 2005/0123672 A1 | 6/2005 | Justin et al. |
| 2005/0154471 A1 | 7/2005 | Aram et al. |
| 2005/0170159 A1 | 8/2005 | Ramsey et al. |
| 2005/0171604 A1 | 8/2005 | Michalow |
| 2005/0177169 A1 | 8/2005 | Fisher et al. |
| 2005/0192672 A1 | 9/2005 | Wyss et al. |
| 2006/0015187 A1 | 1/2006 | Hunter et al. |
| 2006/0045903 A1 | 3/2006 | Kadiyala et al. |
| 2006/0147332 A1 | 7/2006 | Jones et al. |
| 2006/0241776 A1 | 10/2006 | Brown et al. |
| 2006/0254200 A1 | 11/2006 | Clarke et al. |
| 2007/0142914 A1 | 6/2007 | Jones et al. |
| 2007/0156249 A1 | 7/2007 | Lawrynowicz et al. |
| 2007/0225390 A1 | 9/2007 | Wang et al. |
| 2008/0004709 A1 | 1/2008 | O'Neill et al. |
| 2008/0050412 A1 | 2/2008 | Jones et al. |
| 2008/0161927 A1 | 7/2008 | Savage et al. |
| 2008/0288083 A1 | 11/2008 | Axelsson et al. |
| 2009/0068245 A1 | 3/2009 | Noble et al. |
| 2009/0087605 A1 | 4/2009 | Ramsey et al. |
| 2009/0112315 A1 | 4/2009 | Fang et al. |
| 2010/0057211 A1 | 3/2010 | Cuckler et al. |
| 2011/0076316 A1 | 3/2011 | Sivananthan et al. |
| 2012/0067853 A1 | 3/2012 | Wang et al. |
| 2012/0148987 A1 | 6/2012 | Dolabdjian et al. |
| 2012/0245697 A1 | 9/2012 | Hunter et al. |
| 2013/0056912 A1 | 3/2013 | O'Neill et al. |
| 2013/0123935 A1 | 5/2013 | Hunt et al. |
| 2013/0158672 A1 | 6/2013 | Hunt |
| 2013/0218282 A1 | 8/2013 | Hunt |
| 2014/0058526 A1 | 2/2014 | Meridew et al. |
| 2014/0121776 A1 | 5/2014 | Hunt |
| 2014/0277548 A1 | 9/2014 | Cohen et al. |
| 2014/0288649 A1 | 9/2014 | Hunt |
| 2014/0288650 A1 | 9/2014 | Hunt |
| 2014/0343681 A1 | 11/2014 | Cohen et al. |

FOREIGN PATENT DOCUMENTS

| | | |
|---|---|---|
| CN | 102087676 A | 6/2011 |
| DE | 19502733 A1 | 3/1996 |
| EP | 0 178 650 A2 | 4/1986 |
| EP | 0295038 A2 | 12/1988 |
| EP | 0 528 800 A1 | 3/1993 |
| EP | 0761242 A1 | 3/1997 |
| EP | 1247537 A1 | 10/2002 |
| EP | 1 300 511 A2 | 4/2003 |
| EP | 1418013 A1 | 5/2004 |
| EP | 1426013 A1 | 6/2004 |
| EP | 1455666 A1 | 9/2004 |
| EP | 1493455 A2 | 1/2005 |
| EP | 1683593 A2 | 7/2006 |
| EP | 1800700 A2 | 6/2007 |
| EP | 1806154 A1 | 7/2007 |
| EP | 1949989 A1 | 7/2008 |
| JP | 2255329 A | 10/1990 |
| JP | 4041794 A | 2/1992 |
| JP | 11287020 A | 10/1999 |
| JP | 11348045 A | 12/1999 |
| JP | 2001303751 A | 10/2001 |
| JP | 2003293012 A | 10/2003 |
| JP | 2006158953 A | 6/2006 |
| RU | 2218242 C2 | 12/2003 |
| WO | 9606881 A2 | 3/1996 |
| WO | 02085246 A2 | 10/2002 |
| WO | 2005/084216 A2 | 9/2005 |
| WO | 2005080029 A1 | 9/2005 |
| WO | 2005087982 A1 | 9/2005 |
| WO | 2007058160 A1 | 5/2007 |
| WO | 2009116950 A1 | 9/2009 |
| WO | 2011002765 A2 | 1/2011 |
| WO | 2013006778 A2 | 1/2013 |

OTHER PUBLICATIONS

Created and Designed by Shaman Gaspar, Maintained by Peter Fox, "Direct Laser Remelting", "Project Web Site", Using Lasers to Grow 3D object on Stainless Steel; The University of Liverpool 2002; http://mserc.liv.ac.uk/research/dlr/dlr_html.

Dr. Kerron Harvey, producer, Research Intelligence, The University of Liverpool, Issue 13, Jun. 2002.

European Search Report and Written Opinion, EP05028133, dated May 11, 2010.

H.J. Niu and I.T.H. Chang, "Selective Laser Sintering of Gas and Water Atomized High Speed Steel Powders," Scripta Materialia vol. 41, No. 1, (1999), pp. 25-30.

Hawley's Condensed Chemical Dictionary, 14th edition. John Wiley & Sons, 2002. Definition: sintering.

Hollander et al., Structural mechanical and in vitro characterization of individually structured Ti-Al-4V produces by direct layer forming, Biomaterials, pp. 1-9, 2005.

Patello-femoral Arthroplasty X-ray Results, Stryker Howmedica Osteonics, date not known.

R.H. Morgan, A.J. Papworth, C. Sutcliffe, P. Fox, W. O'Neill, "High density net shape components by direct laser re-melting of single phase powders," Journal of Materials Science, 37, (2002), pp. 3093-3100.

The Metals Handbook, Desk Edition, 2nd Edition, ASM International, 1998, p. 29.

Vureal et al., Plasma-sprayed oxide ceramics on steel substrates, Surface Coatings and Technology, 97 (1997) 347-354.

European Search Report and Written Opinion, EP10162970, dated Jun. 17, 2010.

(56) References Cited

OTHER PUBLICATIONS

R. Morgan, C.J. Sutcliffe, W. O'Neill, "Experimental investigation of nanosecond pulsed Nd:YAG laser re-melted pre-placed powder beds," Rapid Prototyping Journal, vol. 7, No. 3, 2001, pp. 159-172.
N.K. Vail, L.D. Swain, W.C. fox, T.B. Aufdlemorte, G. Lee, J.W. Barlow, "Materials for biomedical applications," Materials and Design, 20, 1999, pp. 123-132.
K. Harvey (producer), "Fast masters," Research Intelligence, a publication of the University of Liverpool, Issue 13, Jun. 2002, pp. 1-8.
European Search Report and Written Opinion, EP06127218, dated May 6, 2010.
C.K. Chua et al. Development of a Tissue Engineering Scaffold Structure Library for Rapid Prototyping. Parts 1 and 2, International Journal of Advanced Manufacturing Technology, (2003) vol. 21, pp. 291-312.
Meiners W, Over C, Wissenbach K, Poprawe R., Direct generation of metal parts and tools by selective laser powder remelting (SLPR). Proceedings of SFF, Austin, Texas, Aug. 9-11, 1999.
PCT/US2008/008955 International Preliminary Report on Patentability mailed Feb. 4, 2010.
PCT/US2008/008955 International Search Report and Written Opinion mailed Dec. 2, 2008.
"Solid Freeform Fabrication", IEEE Spectrum, Feb. 1999, pp. 34-43.
Australian Examination Report for Application No. 2013202075 dated Feb. 13, 2015.
Australian Examination Report for Application No. 2013202686 date Aug. 7, 2014.
Canadian Office Action and Examination Search Report for Appln. No. 2,860,188 dated Jun. 4, 2015.
Chen, 3D Texture Mapping for Rapid Manufacturing, University of Southern California, 2007.
Custom Design and Manufacturing of Canine Knee Implants,<http://www.lib.ncsu.edu/resolver/1840.16/670>, Issued Dec. 2, 2003.
Engelbrecht et al., Cellular Structures for Optimal Performance, Georgia Institute of Technology & Paramount Industries, Inc., 2009.
Wang, Computer-Aided Design Methods for Additive Fabrication of Truss Structures, Georgia Institute of Technology, 2002.

* cited by examiner

LASER-PRODUCED POROUS STRUCTURE

CROSS-REFERENCE TO RELATED APPLICATIONS

This application is a continuation of U.S. application Ser. No. 11/027,421, filed on Dec. 30, 2004, now abandoned, the disclosure of which is incorporated herein by reference.

BACKGROUND OF THE INVENTION

The present invention relates to a porous surface or structure and a method for forming the same, which uses a directed energy beam to selectively remelt a powder to produce a part. The energy beam may include a laser beam, and an electron beam or the like. In particular, this invention relates to a computer-aided laser apparatus, which sequentially remelts a plurality of powder layers to form unit cells to build the designed part in a layer-by-layer fashion. The present application is particularly directed toward a method of forming a porous and partially porous metallic structure.

The field of free-form fabrication has seen many important recent advances in the fabrication of articles directly from computer controlled databases. These advances, many of which are in the field of rapid prototyping of articles such as prototype parts and mold dies, have greatly reduced the time and expense required to fabricate articles, particularly in contrast to conventional machining processes in which a block of material, such as a metal, is machined according to engineering drawings.

One example of a modern rapid prototyping technology is the selective laser sintering process practiced by systems available from 3D Systems Valencia Calif. According to this technology, articles are produced in layer-wise fashion from a laser-fusible powder that is dispensed one layer at a time. The powder is fused, remelted or sintered, by the application of laser energy that is directed in raster-scan fashion to portions of the powder layer corresponding to a cross section of the article. After the fusing of the powder on one particular layer, an additional layer of powder is dispensed, and the process repeated, with fusion taking place between the current layer and the previously laid layers until the article is complete. Detailed descriptions of the selective laser sintering technology may be found in U.S. Pat. No. 4,863,538, U.S. Pat. No. 5,017,753, U.S. Pat. No. 5,076,869 and U.S. Pat. No. 4,944,817. The selective laser remelting and sintering technologies have enabled the direct manufacture of solid or dense three-dimensional articles of high resolution and dimensional accuracy from a variety of materials including wax, metal powders with binders, polycarbonate, nylon, other plastics and composite materials, such as polymer-coated metals and ceramics.

The field of the rapid prototyping of parts has, in recent years, made large improvements in broadening high strain, high density, parts for use in the design and pilot production of many useful articles, including metal parts. These advances have permitted the selective laser remelting and sintering processes to now also be used in fabricating prototype tooling for injection molding, with expected tool life in access of ten thousand mold cycles. The technologies have also been applied to the direct fabrication of articles, such as molds, from metal powders without a binder. Examples of metal powder reportedly used in such direct fabrication include two-phase metal powders of the copper-tins, copper-solder (the solder being 70% lead and 30% tin), and bronze-nickel systems. The metal articles formed in these ways have been quite dense, for example, having densities of up to 70% to 80% of fully dense (prior to any infiltration). Prior applications of this technology have strived to increase the density of the metal structures formed by the melting or sintering processes. The field of rapid prototyping of parts has focused on providing high strength, high density, parts for use and design in production of many useful articles, including metal parts.

However, while the field of rapid prototyping has focused on increasing density of such three-dimensional structures, the field has not focused its attention on reducing the density of three-dimensional structures. Consequently, applications where porous and partially porous metallic structures, and more particularly metal porous structures with interconnected porosity, are advantageous for use have been largely ignored. One such reference which hasn't ignored metal porous structures with interconnected porosity and having a relatively low density is commonly assigned U.S. patent application Ser. No. 10/704,270 filed on Nov. 7, 2003, the disclosure of which is hereby incorporated herein by reference. Although this reference has provided various techniques in creating laser produced porous surfaces, still greater technologies are needed in this area.

In either case, the present invention is equally adapted for building porous structure having a high density or a low density.

SUMMARY OF THE INVENTION

The present invention provides a method for building various structures and surfaces but specifically medical implants. The structures are built in a layer-by-layer fashion with individual layers including portions of predetermined unit cells.

In one embodiment of the present invention, a layer of metal powder is deposited on a substrate. The substrate may be a work platform or a base, with the base or core being provided to possibly be an integral part of the finished product. After an individual layer of powder is deposited a scanning process may be preformed to selectively melt the powder to form portions of a plurality of predetermined unit cells. The scanning process includes scanning a laser beam onto the metal powder.

As successive layers are deposited and scanned a structure is built form one end to an opposite end. The structure includes a plurality of predetermined unit cells. The unit cells provide the structure with interconnecting pores as well as porosity. The size of the pores and porosity as well as other factors may all be predetermined.

In one preferred embodiment the size of the pores of the porosity of the built structure are specifically chosen to provide the structure with characteristics similar to medical implants.

In one aspect of the present invention disclosed is a method of producing a three-dimensional porous tissue in-growth structure. The method preferably includes depositing a first layer of a powder made from a metal selected from the group consisting of titanium, titanium alloys, stainless steel, cobalt chrome alloys, tantalum and niobium onto a substrate. The layer of powder is than scanned using a laser beam. The laser beam has a power, and scans the powder layer for a period of time with a point distance. The power of the laser beam is preferably within the range of 5 to 1000 watts although the present invention may be adapted for different power ranges. Additionally, in a preferred embodiment, the exposure time is in a range between 100 µsec to 1000 µsec. The laser beam scans the powder layer to form a portion of a plurality of predetermined unit cells. The predetermined unit cells include struts having cross-sectional dimensions. The cross-section of the struts may be any regular of irregular shape. A few such examples include, circular, rectangular, cubic cross-sections or the like.

In one preferred embodiment of the present invention the laser power is 90.5 W, the exposure time is 1000 μsec and the point distance is 90 μm.

The method also preferably includes depositing at least one additional layer of the powder onto the first layer and repeating the step of scanning the additional layers with a laser beam for at least one of the deposited layers in order to continuing forming the predetermined unit cells.

The predetermined unit cells make take the shape of most regular or irregular structure. For example, the unit cells may be in the shape of a tetrahedron, dodecahedron or octahedron as well as other symmetrical structures. As mentioned, the unit cells may not have such uniformity and have an irregular shape. The unit cells may also be truncated, which includes eliminating some of the struts, which form a unit cell. Truncated unit cells located at the exterior surface of a built product provide a barbed effect to the product.

In a preferred embodiment of the present invention, the layers of metal powder have a thickness between 5 μm to 2000 μm.

The present invention may also include predetermining a porosity range for at least one deposited powder layer and scanning the layer in a manner to provide the deposited layer with porosity within the predetermined porosity range.

In one aspect of the present invention, the substrate may include a base, core, work platform or the like. As with the layer of powder, the metal selected to form the base or core may be selected from the group consisting of titanium, titanium alloys, stainless steel, cobalt chrome alloys, tantalum and niobium. Portions of the powder layers may be fused and or sintered to the base or core. The base or core may either be separated from the finished built product or may be an integral part of the finished product. If the base or core is an integral part of the finished product it may impart additional physical properties to the overall construct. The base or core may be constructed using the present invention.

In one aspect of the present invention a solid or semipervious layer may be placed between the substrate and the first deposited powder layer.

In another aspect of the present invention during the at least one of the steps of the scanning process, a plurality of satellites may be formed on portions of the predetermined unit cells. The satellites may remain attached to the predetermined unit cells so as to affect the porosity of the structure. In an alternate embodiment, the satellites may be removed. One way to remove the satellites is by an acid etching process. The acid etching process may be conducted not only to remove some of all of the satellites but also to alter the cross-sectional dimensions of various struts forming the predetermined unit cells.

In another aspect of the present invention, a plurality of struts may intersect at an intersection point. Either prior to completion of after completion of the finished structure, various intersection points may be sintered. In one reason for sintering the intersection points is to eliminate any unmelted metal powder spots.

In a preferred aspect of the present invention, the laser beam may be adjusted to modify the length and/or cross-section of various struts. Additionally, at least some of the unit cells may be deformed so as to drape over the substrate. Laser beam compensation may also be employed. Some of the struts of the unit cells may overlap struts of other unit cells. This aspect also enables the adjusting of the porosity throughout the completed structure.

At least some of the predetermined unit cells may be coated with unmelted metal particles.

In one aspect of the present invention the metal powder layers are deposited and scanned in order to form a medical implant. The medical implant preferably having porosity within a predetermined range. The medical implant may include an acetabular cup, acetabular shell, a knee implant, femoral or hip implant or the like. The constructed medical implant may have a porosity, which promotes bone ingrowth and/or provides the medical implant with soft tissue characteristics.

The medical implants, as well as other constructed structures, may be provided with an attaching mechanism for anchoring or at least more firmly attaching the medical implant to another element. One such example is an acetabular shell being provided with a rim to snap-fit to an acetabular cup.

In another aspect of the invention, the structure may be subjected to a hot isostatic pressing.

In one preferred embodiment of the present invention, the method of producing a three-dimensional construct includes loading a file of a component into an engineering design package. The component is scaled down in the file from its original size. A Boolean operation is next performed to subtract the scaled down component from the original component. This creates a jacket. The jacket can than be processed using a bespoke application that populates the jacket with a repeating open cellular structure.

The open cellular structure is than sliced using the bespoke application to a predetermine thickness.

The main body of the file component jacket is loaded into a user interface program and the jacket is sliced into layers having a predetermined thickness. Hatching is than applied to the file component jacket as required to build a construct and the jacket is merged with the open cellular lattice structure. Once a representation has been obtained the depositing and scanning steps of the present invention may be conducted to build the final product.

BRIEF DESCRIPTION OF THE DRAWINGS

Methods of forming the porous surface of the present invention can be performed in many ways and some embodiments will now be described by way of example and with reference to the accompanying drawings in which.

DETAILED DESCRIPTION OF THE INVENTION

Figure 1A:
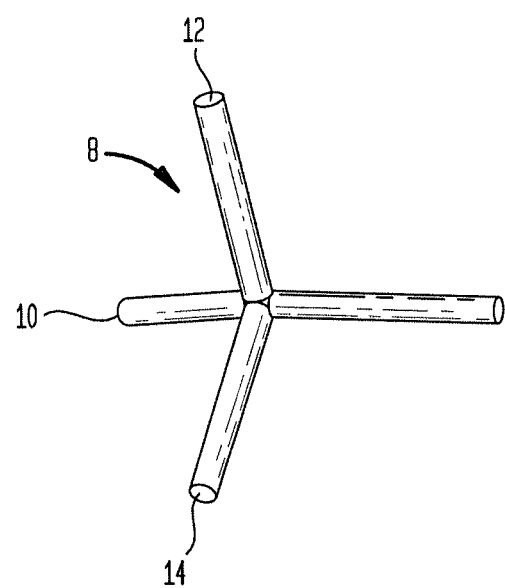
FIG. 1A illustrates one embodiment of a unit cell of the present invention.

This invention relates to a method of forming porous and partially porous metallic structures which are particularly but not exclusively applicable for use in hard or soft tissue interlock structures for medical implants and prosthesis. The method makes use of laser technology by employing a variety of scanning strategies. Typical metal and metal alloys employed include stainless steel, cobalt chromium alloys, titanium and its alloys, tantalum and niobium, all of which have been used in medical device applications. This invention can be used for such medical device applications where bone and soft tissue interlock with the component is required, or where a controlled structure is required to more closely match the mechanical properties of the device with surrounding tissue.

The intention of the present invention is to produce a three-dimensional structure using a laser remelting process, for example, for building structures utilizing unit cells with or without a solid base or core. When applied to an orthopedic prosthesis, the three-dimensional structure could be used to provide a porous outer layer to form a bone in-growth structure. Alternatively, the porous structure, when applied to a core, could be used to form a prosthesis with a defined stiffness to both fulfill the requirement of a modulus match with surrounding tissue and provide interconnected porosity for tissue interlock. A further use could be to form an all-porous structure with grade pore size to interact with more than one type of tissue. Again, the process can be used to build on a solid base or core with an outer porous surface, the porosity of which is constant or which varies. The base or core materials to which the process is applied may be either titanium and its alloys, stainless steel, cobalt chrome alloys, tantalum or niobium as well as any other suitable material. The preferred surface coatings are titanium, cobalt chrome and tantalum but both stainless steel and niobium can also be used as well as any other suitable material. Fully porous structures may be built from any of the materials tested, with the preferred material being titanium. The intention of the invention is to produce a method which can be exploited on a commercial basis for the production of, for example, bone interlock surfaces on a device although it has many other uses.

According to the present invention, a method of forming a three-dimensional structure includes building the shape by laser melting powdered Ti and alloys, stainless steel, cobalt chrome alloys, Ta or Nb using a continuous or pulsed laser beam. Individual layers of metal are scanned using a laser. Each layer or portion of a layer is scanned to create a portion of a plurality of predetermined unit cells, as will be described below. Successive layers are deposited onto previous layers and also may be scanned. The scanning and depositing of successive layers continues the building process of the predetermined unit cells. As disclosed herein, by continuing the building process refers not only to a continuation of a unit cell from a previous layer but also a beginning of a new unit cell as well as the completion of a unit cell.

The method can be performed so that the structure is porous and if desired, the pores can be interconnecting to provide an interconnected porosity.

If desired, the method can include using a base or core of cobalt chrome alloy, titanium or alloy, stainless steel, niobium and tantalum, on which to build a porous layer of any one of the aforementioned metals and alloys by laser melting using a continuous or pulsed laser beam. Thus, a mixture of desired mixed materials can be employed.

The method can be applied to an existing article made from cobalt chrome, titanium or alloy, stainless steel, tantalum or niobium, such as an orthopedic implant, to produce a porous outer layer from any of the aforementioned metals or alloys to provide a bone in-growth structure.

The invention can, therefore, include a laser melting process which precludes the requirement for subsequent heat treatment of the structure, thereby preserving the initial mechanical properties of the core or base metal. The equipment used for the manufacture of such a device could be one of many currently available including the MCP Realiszer, the EOS M270, Trumpf Trumaform 250, the Arcam EBM S12 and the like. The laser may also be a custom produced laboratory device.

The method can be applied to produce an all-porous structure using any of the aforementioned metal or metal alloys. Such structures can be used as final products, or further processed to form a useful device for bone or soft tissue in-growth, or as some other function such as that of a lattice to carry cells, for example.

The pore density, pore size and pore size distribution can be controlled from one location on the structure to another. It is important to note that successive powder layers can differ in porosity by varying factors used for laser scanning powder layers. Additionally, the porosity of successive layers of powder can be varied by either creating a specific type of unit cell or manipulating various dimensions of a given unit cell.

To produce a porous surface structure, the nature of the material formed as a result of laser melting of powdered beads is principally dependent on the thermal profile involved (heating rate, soaking time, cooling rate); the condition of the raw material (size and size distribution of powder particles); and atmospheric conditions (reducing, inert or oxidizing chamber gas).

There have been a number of studies to determine the optimum pore structure for maximization of bone in-growth on prostheses. The general findings suggest that optimum porosity is between approximately 20% and 40%, and aim to mid value with a mean volume percent of voids of about 70%. The preferred pore structure is interconnected, with a minimum pore size between about 80 μm and 100 μm and a maximum pore size between 80 μm and 800 μm. The structured thickness for in-growth is 1.4-1.6 mm, but can be larger or smaller depending on the application.

In the present invention porous structures are built in the form of a plurality of unit cells. Many designs of unit cells are possible to give the shape, type, degree, and size of porosity required. Such unit cell designs can be dodecahedral, octahedral, diamond, as well as many other various shapes. Additionally, besides regular geometric shapes as discussed above the unit cells of the present invention may be configured to have irregular shapes where various sides and dimensions have little if any repeating sequences. The unit cells can be configured to constructs that closely mimic the structure of trabecular bone for instance. Unit cells can be space filling, all the space within a three-dimensional object is filled with cells, or interconnected where there may be some space left between cells but the cells are connected together by their edges.

The cells can be distributed within the construct a number of ways. Firstly, they may be made into a block within a computer automated design system where the dimensions correspond to the extent of the solid geometry. This block can then be intersected with the geometry representing the component to produce a porous cellular representation of the geometry. Secondly, the cells may be deformed so as to drape over an object thus allowing the cells to follow the surface of the geometry. Thirdly, the cells can be populated through the geometry following the contours of any selected surface.

The unit cell can be open or complete at the surface of the construct to produce a desired effect. For instance, open cells with truncated lattice struts produce a surface with a porosity and impart the surface with some degree of barb.

Modifying the lattice strut dimensions can control the mechanical strength of the unit cell. This modification can be in a number of key areas. The lattice strut can be adjusted by careful selection of build parameters or specifically by changing the design of the cross-section of each strut. The density of the lattice can similarly be adjusted by modification of the density of the unit cells as can the extent and shape of porosity or a combination thereof. Clearly the overall design of the unit cell will also have a significant effect of the structural performance of the lattice. For instance, dodecahedral unit cells have a different mechanical performance when compared to a tetrahedral (diamond) structure.

Figure 1B:
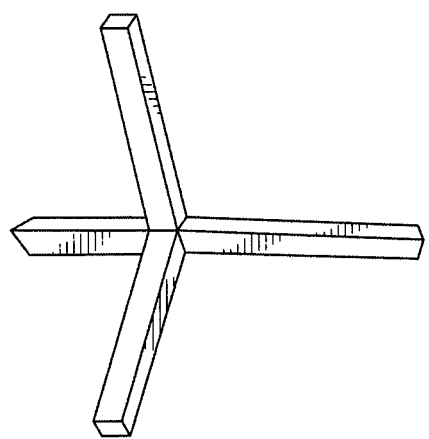
FIG. 1B illustrates an alternate embodiment of a unit cell of the present invention.

As shown in FIGS. 1A and 1B, in a tetrahedron 8, each point 10, 12, 14, and 16 is the same distance from the neighboring point. This structure is analogous to the arrangements of the carbon atoms in diamond.

Each carbon atom in the diamond is surrounded by four nearest neighbors. They are connected together by bonds that separate them by a distance of 1.5445 angstroms. The angles between these bonds are 109.5 degrees. As a result, the central atom and its neighbors form a tetrahedron. This geometry as in the case discussed herein may then be scaled to appropriate value for the pore construct required.

The two key parameters used to define the relations regarding height, surface area, space height, volume of tetrahedron, and the dihedral angle of a tetrahedron are the strand length of the tetrahedron and, i.e., the diameter or height and width, cross section area of the strand i.e., strut. These two parameters control the pore size and porosity of the structure. The parameter editor and relation editor within a typical CAD system can be used to control these parameters. Hence, by changing the parameters one can change the fundamental properties of the porous structure. As shown in FIGS. 1A and 1B, the diamond structure may have a circular cross-section strands or square cross-section strands. Although only two strand cross-sections are illustrated, strands having various cross-sections are possible. Further, this is true with most of the designs for the unit cell.

Figure 1C:
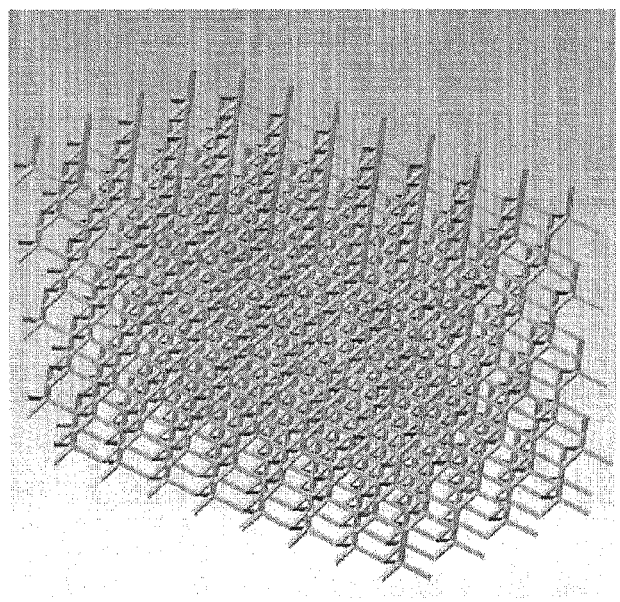
FIG. 1C illustrates a lattice structure formed using a plurality of unit cells illustrated in FIG. 1B.
Figure 2:
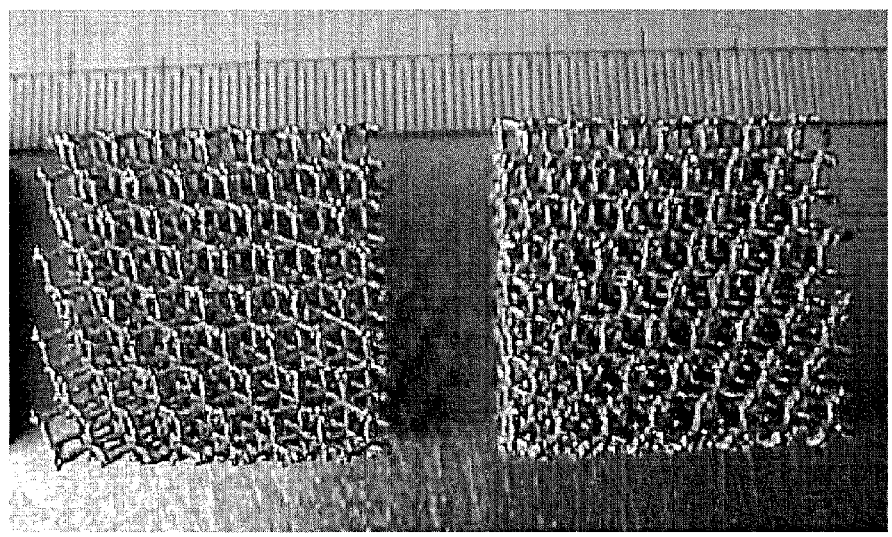
FIG. 2 illustrates lattice structures with and without laser beam compensation formed using the unit cells illustrated in FIG. 1B.

To create the mesh as shown in FIG. 1C, the unit cell can be instanced across the 3-D space to produce the required lattice. FIG. 2 illustrates a view of a diamond lattice structure with and without laser beam compensation. Laser beam compensation essentially allows the diameter of the beam to be taken into account. Without it the constructed geometry is one beam diameter too wide as the beam traces out the contour of the particular section being grown. When laser beam compensation is utilized, the contour is offset half a beam diameter all around the constructed geometry which is represented in the CAD file. Although various parameters may be used, the parameters employed to create the lattices of FIG. 2 include a laser power of 90.5 watts with an exposure time of 1,000 μsec from a point distance of 90 μm. Table 1 illustrates various other examples of parameters that may be used to create various unit cells.

TABLE 1

| | Part build on SLM | | | | |
|---|---|---|---|---|---|
| | edge length μm | diameter μm | laser power Watts | exposure μsec | point distance μm |
| Diamond Structure | 2000 | 200 | 90.5 | 1000 | 90 |
| Diamond Structure with compensation | 2000 | 200 | 90.5 | 1000 | 90 |
| Dodecahedron Structure | 1500 | 200 | 68.3 | 1000 | 90 |
| Dodecahedron Structure with compensation | 1500 | 200 | 68.3 | 1000 | 90 |
| Modified Truncated Octahedron | 1500 | 200 | 90.5 | 1000 | 90 |

Figure 3A:
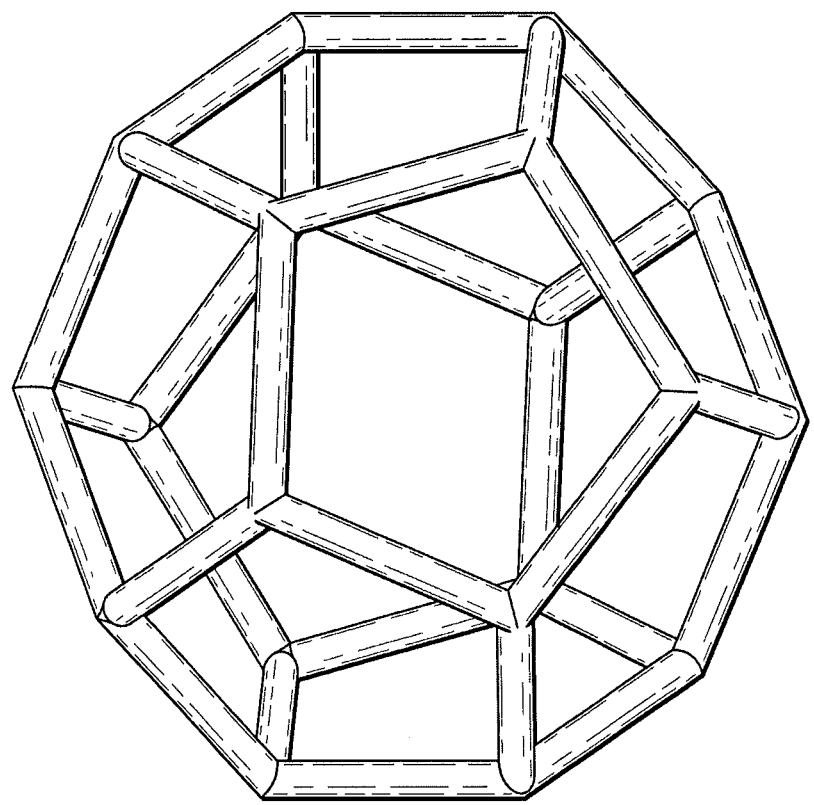
FIG. 3A illustrates an alternate embodiment of a unit cell of the present invention.
Figure 3B:
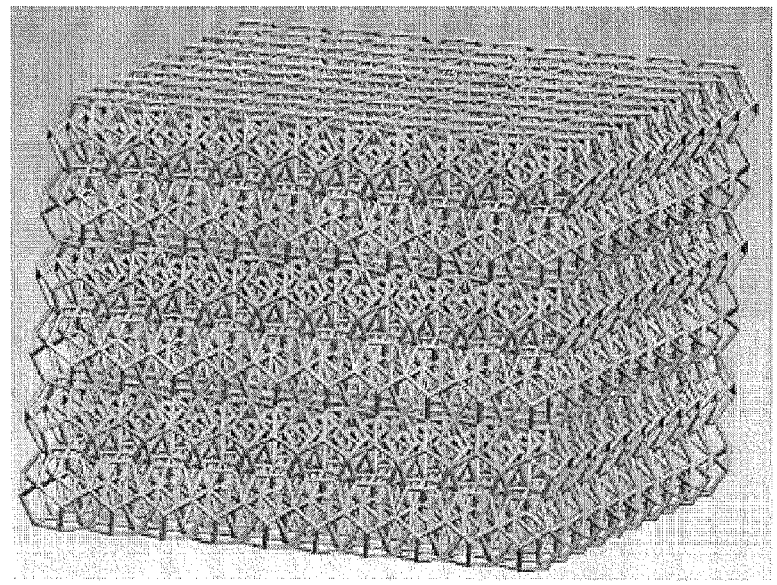
FIG. 3B illustrates a lattice structure formed using a plurality of unit cells illustrated in FIG. 3A.

As shown in FIGS. 3A and 3B, the porous structure can also be created using a unit cell in the shape of a dodecahedron. The regular dodecahedron is a platonic solid composed of 20 polyhydron vertices, 30 polyhydron edges, and 12 pentagonal faces. This polyhydron is one of an order of five regular polyhedra, that is, they each represent the regular division of 3-dimensional space, equilaterally and equiangularly. This basic unit cell for a decahedron mesh can be built up in a CAD package using the following calculations and procedure. The dodecahedron has twelve regular pentagonal faces, twenty vertices, and thirty edges. These faces meet at each vertex. The calculations for a side length of a dodecahedron are given by simple trigonometry calculations and are known by those in the art.

In a method of use, a sweep feature is first used to model the dodecahedron structure by driving a profile along a trajectory curve. The trajectory curves are constructed from datum points corresponding to the vertices of the dodecahedron connected by datum curves. The type of profile remains constant along the sweep producing the model shown in FIG. 3A. The size and shape of the profile can be designed to suit the particular application and the required strut diameter. Once a particular unit cell has been designed, the cell can be instanced to produce a regular lattice as shown in FIG. 3B. As a dodecahedron is not spaced filling, meshes are produced by simple offsetting of the unit cell and allowing some of the struts to overlap. This method of overlapping may be used with the alternate shapes of the unit cell.

Figure 4:
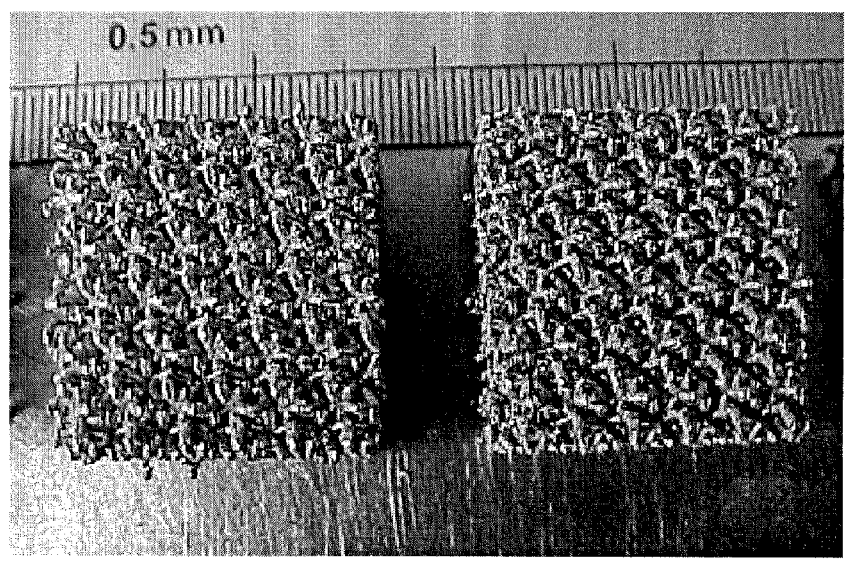
FIG. 4 illustrates lattice structures formed with and without laser beam compensation.

FIG. 4 shows a view of a dodecahedron (with and without laser beam compensation, from left to right) structure using selective laser melting process parameters. Once again, although the parameters may be varied, the lattices of FIG. 4 were created using the following parameters; a laser power of 90.5 watts, exposure of the powder for 1,000 μsec and a point distance of 90 μm.

Figure 5A:
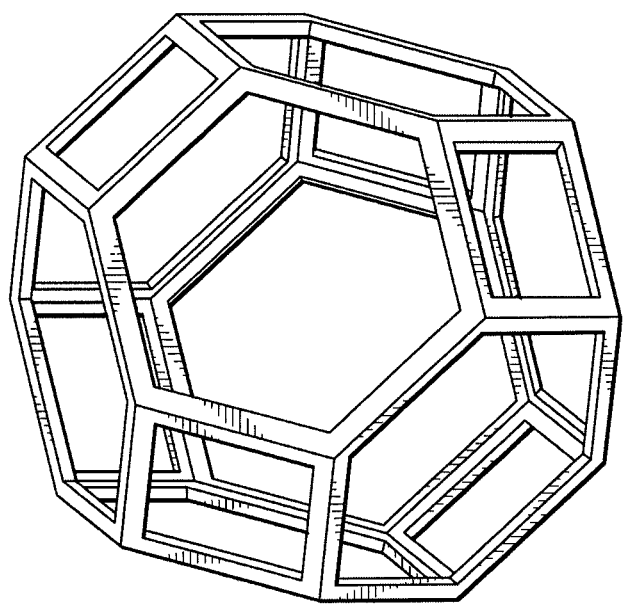
FIG. 5A illustrates an alternate embodiment of a unit cell of the present invention.
Figure 5B:
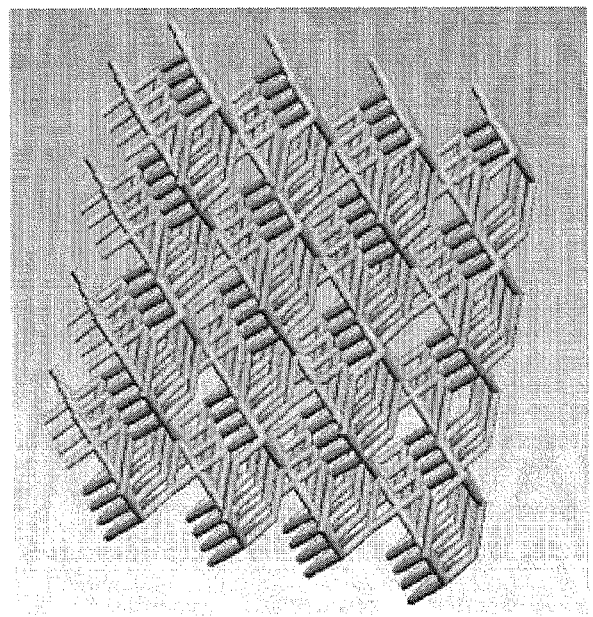
FIG. 5B illustrates a lattice structure formed using a plurality of the unit cells illustrated in FIG. 5A.
Figure 6A:
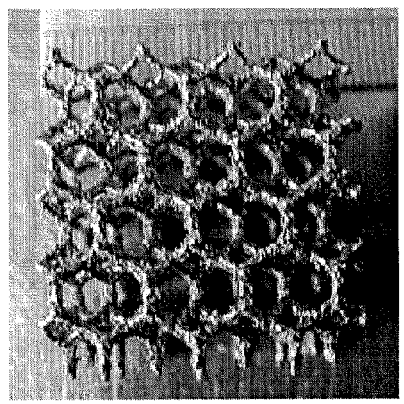
FIGS. 6A and 6B illustrate actual lattice structures formed using a plurality of unit cells represented in FIG. 5A.
Figure 6B:
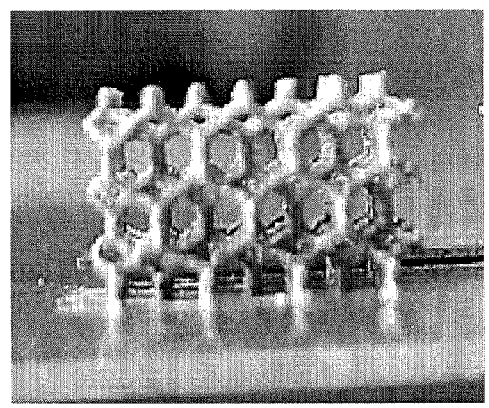

As shown in FIGS. 5A and 5B, the unit cell of the present invention may also be constructed in the shape of a truncated octahedron. A truncated octahedron has eight regular hexagonal faces, six regular square faces, twenty-four vertices, and thirty-six edges. A square and two hexagons meet at each vertex. When the octahedron is truncated, it creates a square face replacing the vertex, and changes the triangular face to a hexagonal face. This solid contains six square faces and eight hexagonal faces. The square faces replace the vertices and thus this leads to the formation of the hexagonal faces. It should be noted here that these truncations are not regular polydra, but rather square-based prisms. All edges of an archamedian solid have the same length, since the features are regular polygons and the edges of a regular polygon have the same length. The neighbors of a polygon must have the same edge length, therefore also the neighbors and so on. As with previous unit cells, various dimensions such as the octahedron height, octahedron volume, octahedron surface area, octahedron dihydral angle, and truncated octahedron volume, truncated octahedron height, truncated octahedron area, truncated octahedron volume, truncated octahedron dihydral angle can be determined by simple trigonometry and are known by those skilled in the art.

Figure 7A:
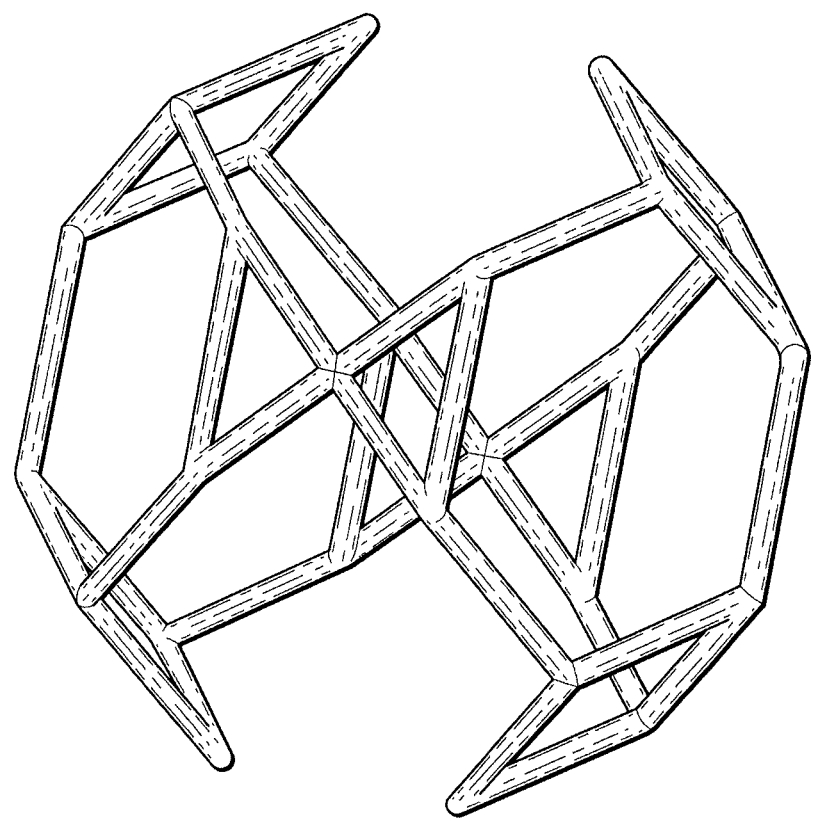
FIG. 7A illustrates an additional embodiment of a unit cell of the present invention.
Figure 7B:
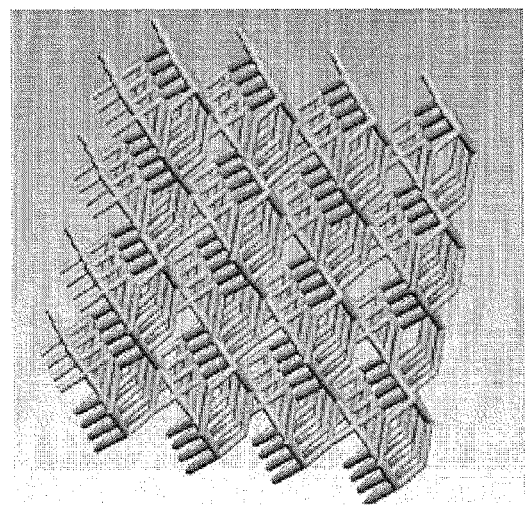
FIG. 7B illustrates a lattice structure created using a plurality of unit cells illustrated in FIG. 7A.

In a method of use, a CAD model of the truncated octahedron is constructed using the sweep feature and calculations and dimensions are incorporated using basic trigonometry. Two tessellate the unit cell, the unit cell is first reoriented to enable easy tessellation and to reduce the number of horizontal struts in the model. Further, the model can be modified to remove all of the horizontal struts as shown in FIG. 7A. The modified structure is reproduced in order to save file size in the Steriolithography ("STL") format of the program. Next, in order to create the unit cells, the method of using a laser melting process is performed. In one preferred embodiment, the parameter chosen includes a laser power of 90.5 watts, an exposure of 1000 μsec with a point distance of 90 μm. FIG. 7b illustrates a lattice structure formed using a plurality of individual truncated octahedron. As discussed earlier, the removal of various struts can create a barb effect on the exterior surface of the lattice structure.

Figure 8A:
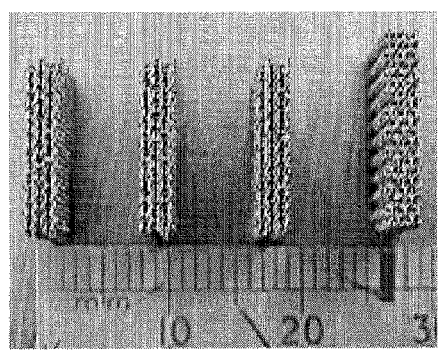
FIG. 8A illustrates lattice structures created using unit cells illustrated in FIG. 7A with varying exposure time.
Figure 8B:
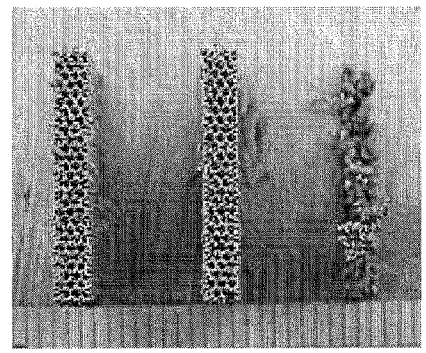
FIG. 8B illustrates lattice structures created using unit cells illustrated in FIG. 1A with varying exposure time.
Figure 8C:
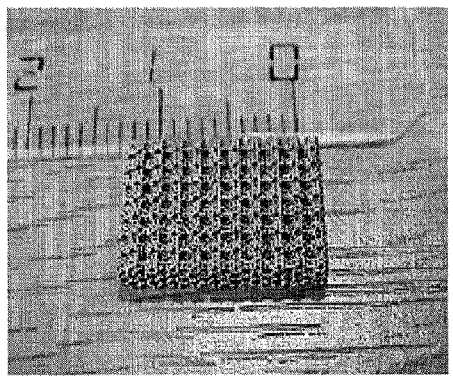
FIG. 8C illustrates a side view of an embodiment of FIG. 8A.
Figure 8D:
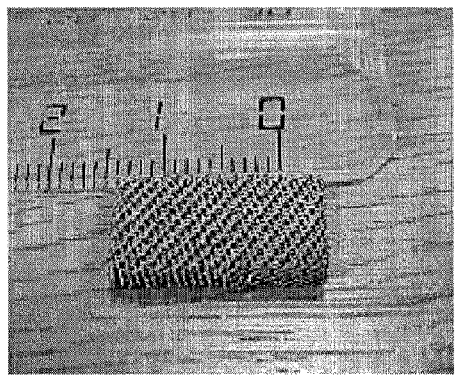
FIG. 8D illustrates a side view of a lattice structure illustrated in FIG. 8B.

As shown in FIGS. 8A-D, it is possible to reduce the size of the unit cell geometry. Also as shown, it is possible to manufacture open cell structures with unit cell sizes below millimeter. FIG. 8A illustrates truncated octahedron structures manufactured using the laser melting process. All the structures were created using a laser power of 90.5 W, and a point distance of 90 μm; however, from left to right, the exposure time was varied from 500 μsec and 100 μsec. FIG. 8b illustrates similar structures and parameters as used with FIG. 8A, however, the unit cell used to create the lattice is diamond. FIGS. 8C and 8D illustrate a side view of the truncated octahedron structure of FIG. 8A and the diamond structure of FIG. 8B, respectively. Table 2 includes various manufacturing parameters used to construct various unit cell structure.

TABLE 2

| | Part build on SLM | | | | | |
|---|---|---|---|---|---|---|
| | Strand length μm | Length of strand c/s μm | Width of strand c/s μm | Laser Power Watts | Exposure μsec | Point distance μm |
| Truncated Octahedron | 3000 | 50 | 50 | 90.5 | 500 | 90 |
| Truncated Octahedron | 3000 | 50 | 50 | 90.5 | 300 | 90 |
| Truncated Octahedron | 3000 | 50 | 50 | 90.5 | 100 | 90 |
| Truncated Octahedron | 1000 | 50 | 50 | 90.5 | 500 | 90 |
| Truncated Octahedron | 1000 | 50 | 50 | 90.5 | 300 | 90 |
| Truncated Octahedron | 1000 | 50 | 50 | 90.5 | 100 | 90 |
| Diamond Structure | 700 | 50 | 50 | 90.5 | 500 | 90 |
| Diamond Structure | 700 | 50 | 50 | 90.5 | 300 | 90 |
| Diamond Structure | 700 | 50 | 50 | 90.5 | 100 | 90 |

Figure 9:
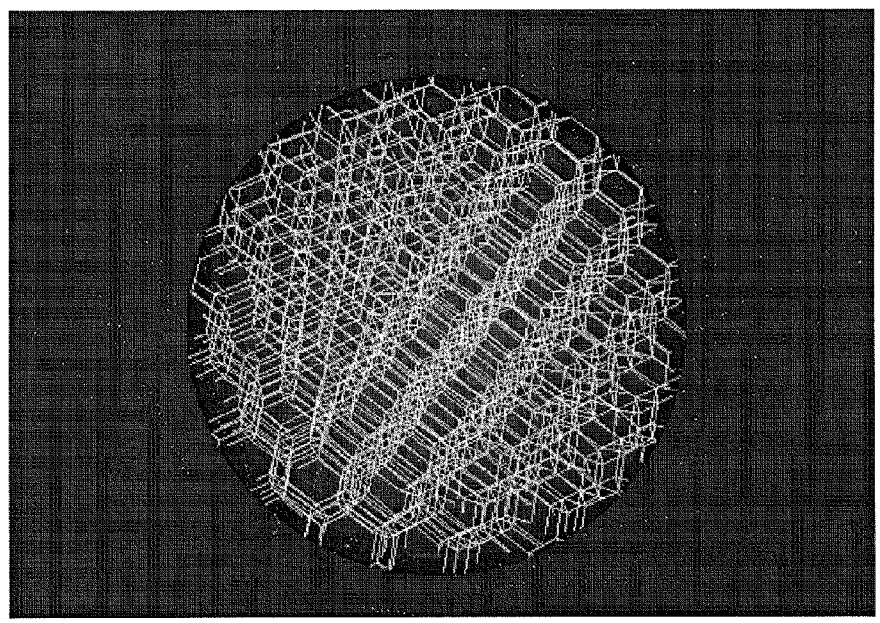
FIG. 9 is a representation of a lattice structure created using a plurality of the unit cells illustrated in FIG. 7A with random perturbation.
Figure 10:
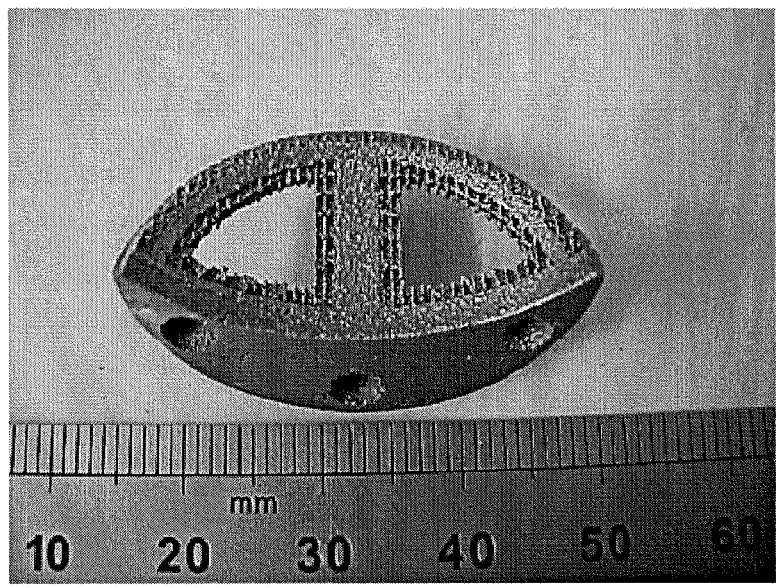
FIG. 10 illustrates graduation of a solid to a lattice build.
Figure 11:
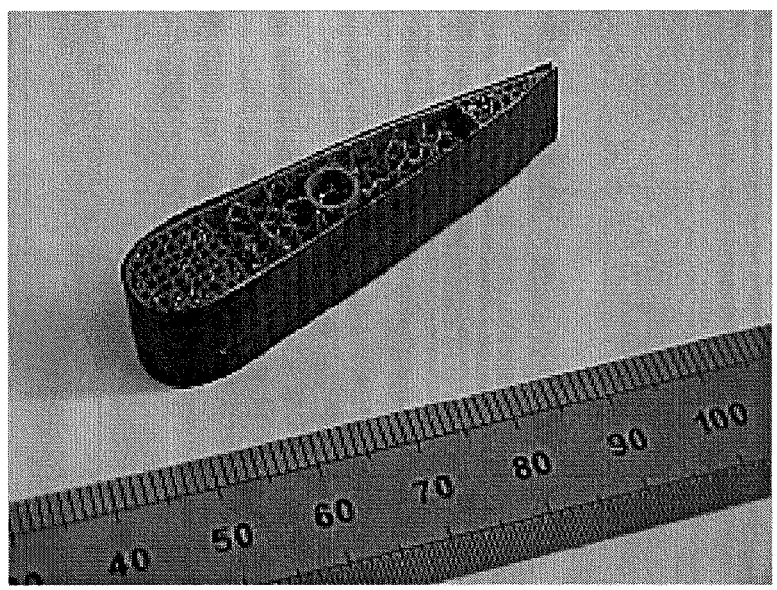
FIG. 11 illustrates a graduation from one lattice density to another.

Random representative geometries may be made from the current regular unit cells by applying a random X, Y, Z perturbation to the vertices of the unit cells. One such example can be seen in FIG. 9. In another aspect of the present invention, various freestanding constructs can be generated. In a typical manufacturing procedure for the production of a construct, in this case a femoral hip component, the laser melting of appropriate metallic powders is employed. Table 3 listed below, includes various examples of equipment and material used in the construct, as well as typical software utilized.

TABLE 3

| Equipment/Software | Description |
| --- | --- |
| Magics V8.05 (Materialise) | CAD software package used for manipulating STL files and preparing builds for Rapid Manufacture (RM) |
| Python | Programming language |
| MCP Realizer | SLM machine using 100 w fibre laser |
| 316 L gas atomized metal powder Osprey Metal Powders Ltd | Metal powder with an mean particle size of approximately 40 μm |

Figure 12A:
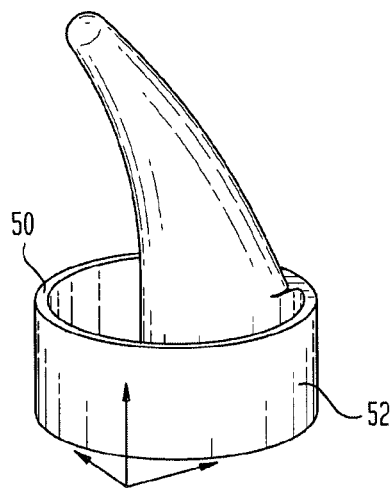
FIG. 12A illustrates a femoral hip component.
Figure 12B:
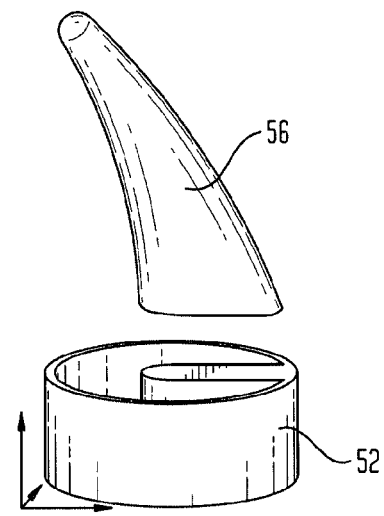
FIG. 12B illustrates an exploded view of FIG. 12A.
Figure 13:
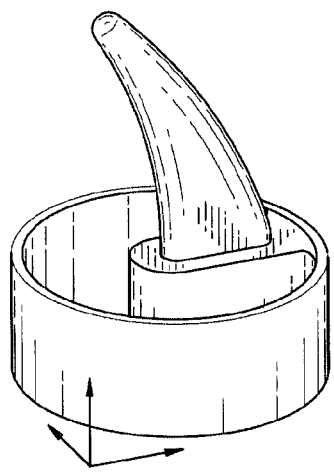
FIG. 13 illustrates the component of FIG. 12A with a reduced sized femoral attachment.
Figure 14:
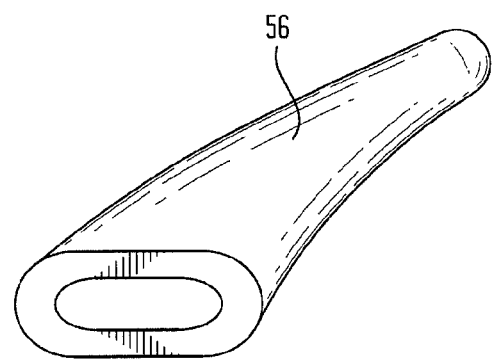
FIG. 14 illustrates a "jacket" created by the subtraction of the embodiment of FIG. 13 from the embodiment of FIG. 12A.

In one example of this procedure an STL file of hip component 50 is loaded into an engineering design package such as Magics, as shown in FIG. 12A. The femoral attachment 51 may then be segmented from the body 52 of the construct. The femoral attachment 51 may then be scaled down to 80% of its original size and reattached to the body 52 of the implant 50 as shown in FIG. 13. This permits the implant to act as a structural core for the surface coating. The selection of the amount of scaling or indeed the design of the core allows for the production of the required structural properties of the stem. Thus, the core may either be scaled down even more or less to meet the required needs of the implant. A Boolean operation may next be performed in Magics to subtract the reduced femoral attachment from the original. This creates a "jacket" 56 i.e., mold to be used as the interconnecting porous construct as shown in FIG. 14.

Figure 15A:
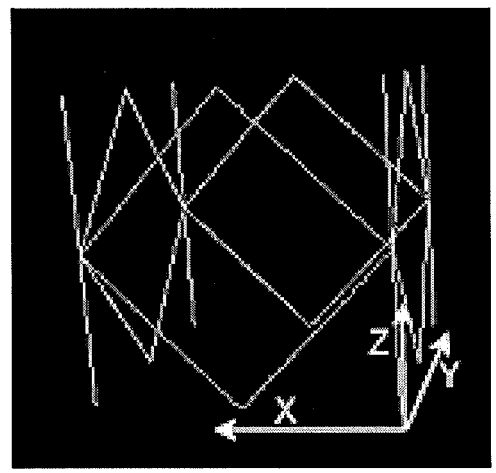
FIG. 15A illustrates one embodiment of a single unit cell for use in an open cellular lattice structure.
Figure 15B:
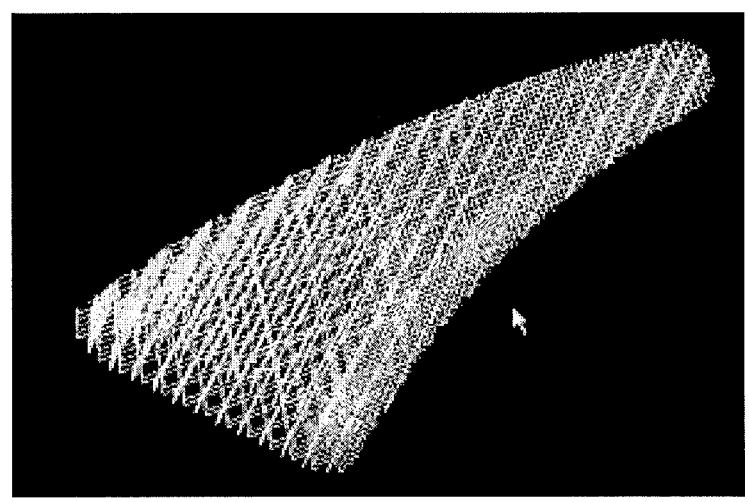
FIG. 15B illustrates an open cellular lattice structure.
Figure 16:
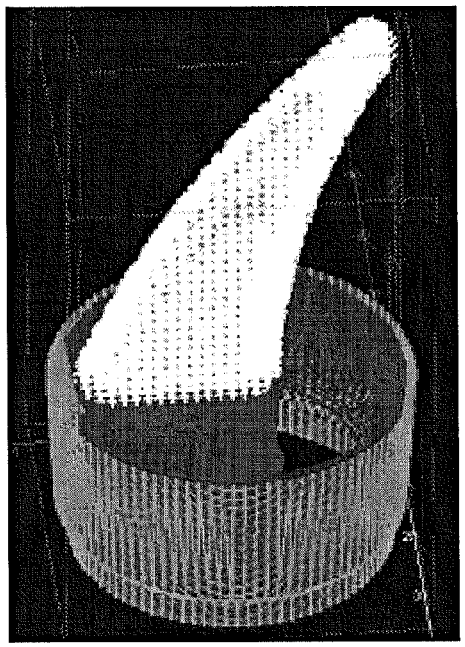
FIG. 16 illustrates the embodiment illustrated in FIG. 15B merged with the embodiment illustrated in FIG. 13.

Jacket 56 is processed via a bespoke application that populates STL shapes with repeating open cellular lattice structures (OCLS). The OCLS used in this instance is a repeating unit cell of size 1.25 millimeters and strand diameter 200 μm. FIG. 15A illustrates a representation of a single unit cell of the OCLS which will be used to populate jacket 56. The OCLS "jacket" 56 as shown in FIG. 15b will act as the porous surface coating of the femoral attachment 50. Once produced, the OCLS is sliced using a bespoke program written in the Python programming language with a layer thickness of 50 μm. The main body of the construct is then loaded into Fusco, a user interface for the MCP realizer. The file is then prepared for manufacture by slicing the file with a 50 μm layer thickness and applying the hatching necessary for building solid constructs. The component and OCLS femoral coating are then merged as shown in FIG. 16. The component may then be built on the SLM system as shown in FIG. 17 with typical process parameters being shown in table 4 below.

TABLE 4

| | Feature | | | | |
| --- | --- | --- | --- | --- | --- |
| | Slice height (μm) | Power (watts) | Exposure (μs) | $P_{dist}$ (μm) | $H_{dist}$ (mm) |
| Solid layer | 100 | 90.5 | 800 | 80 | 0.125 |
| Porous layer | 100 | 90.5 | 3500 | N/a (spot) | N/a |

Figure 17A:
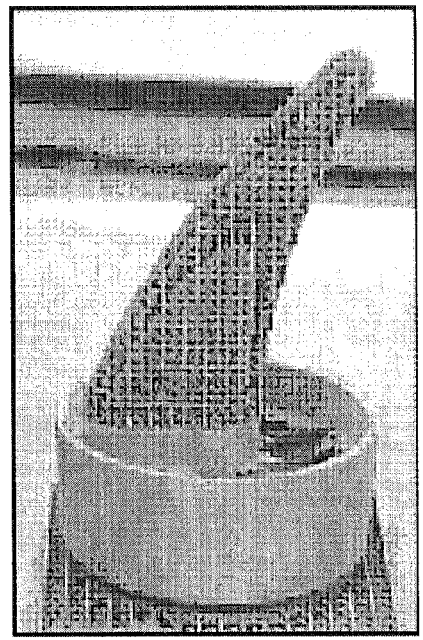
FIGS. 17A and 17B illustrate one embodiment of a finished product.
Figure 17B:
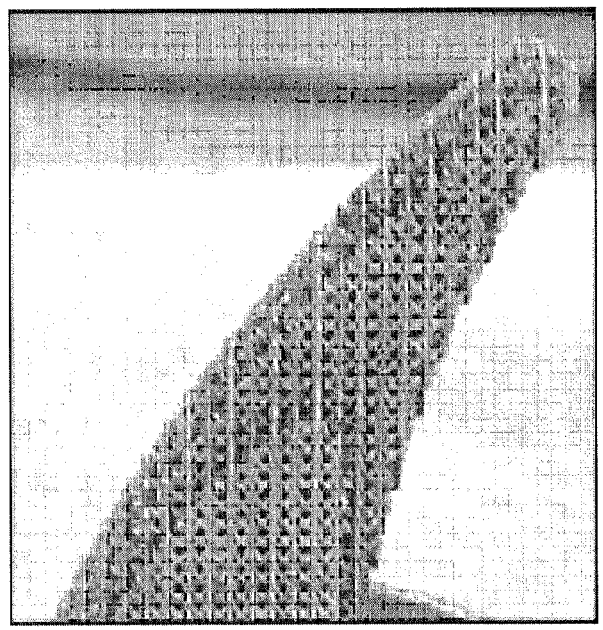
Figure 18A:
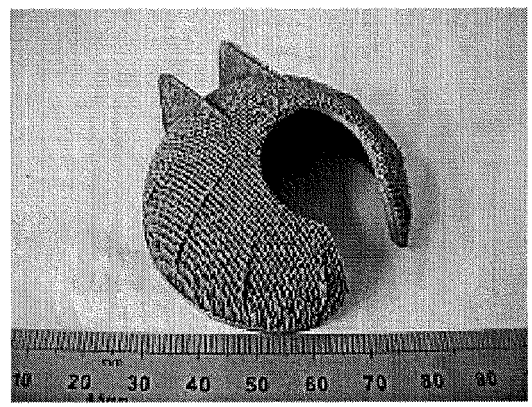
FIGS. 18A-C illustrate an alternate embodiment of a finished product.
Figure 18B:
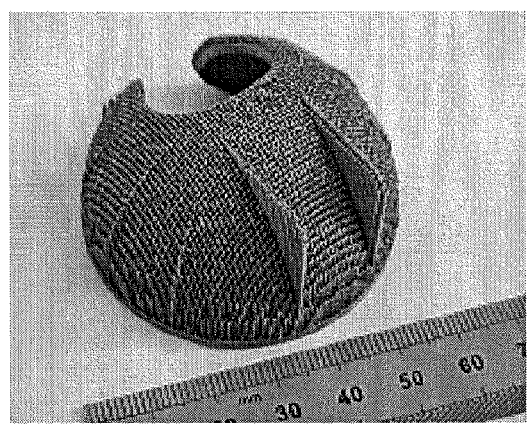
Figure 18C:
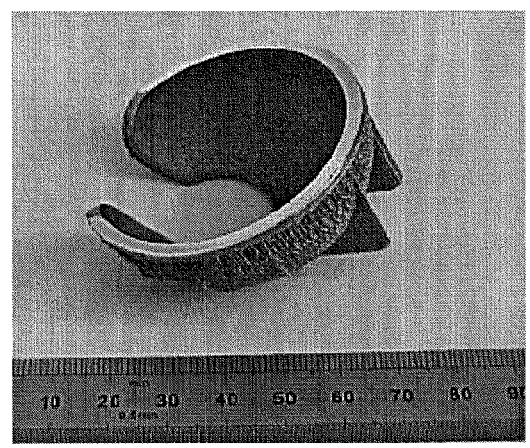
Figure 19A:
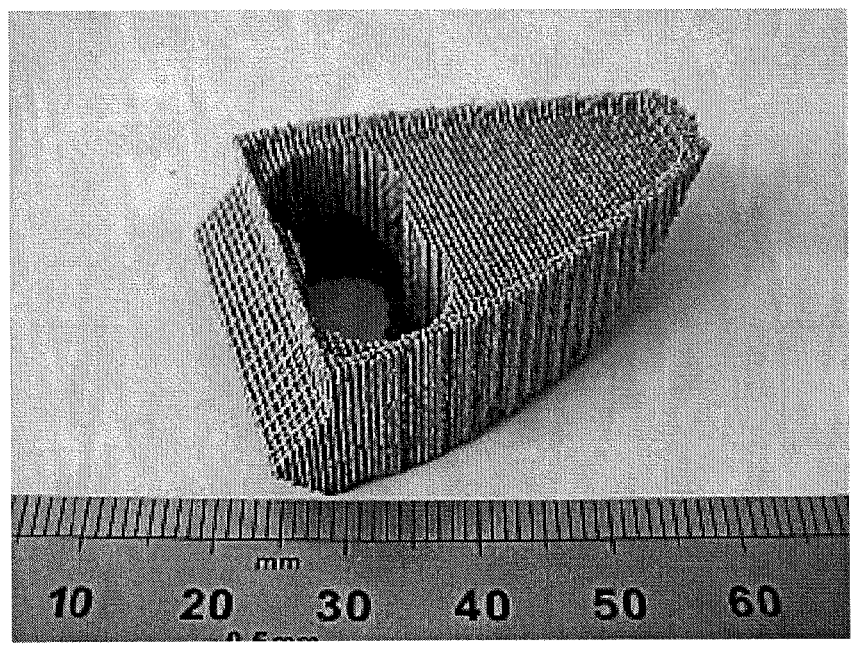
FIGS. 19A and 19B illustrate an alternate embodiment of a finished product.
Figure 19B:
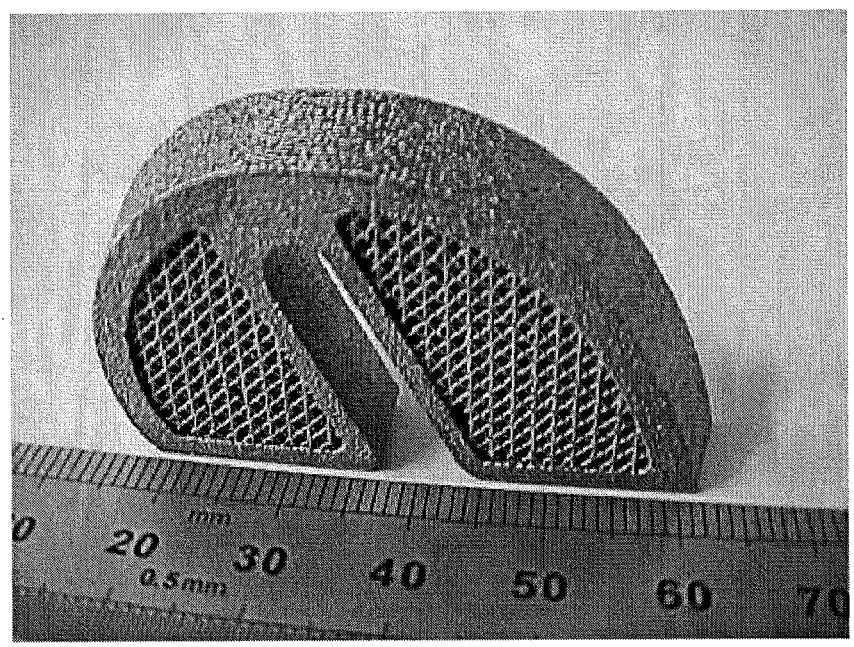
Figure 20A:
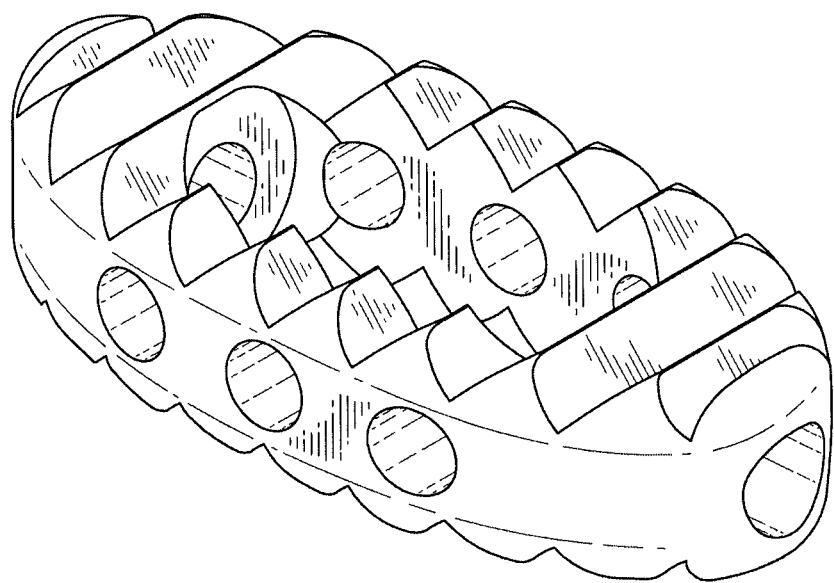
FIGS. 20A-C illustrate an alternate embodiment of a finished product.
Figure 20B:
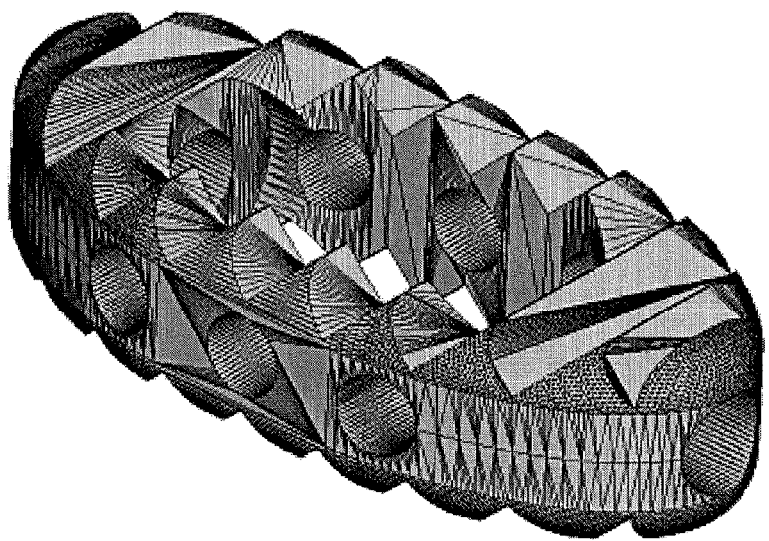
Figure 20C:
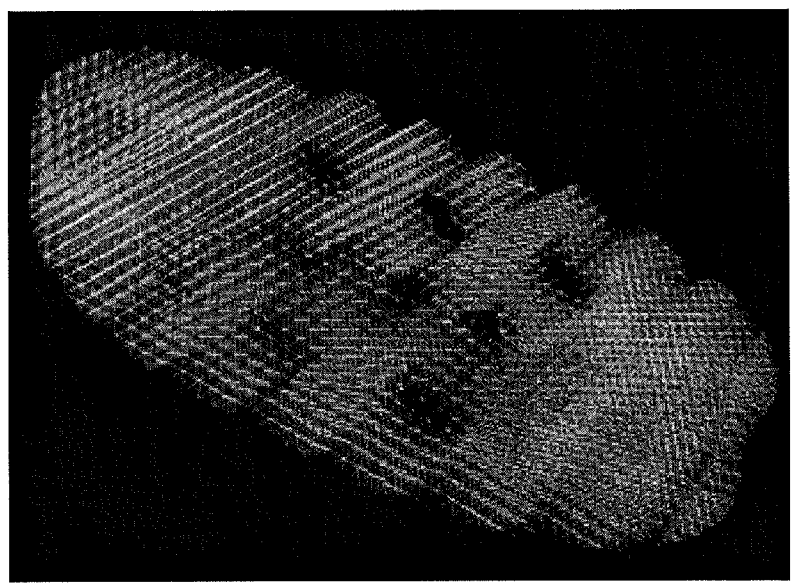
Figure 21A:
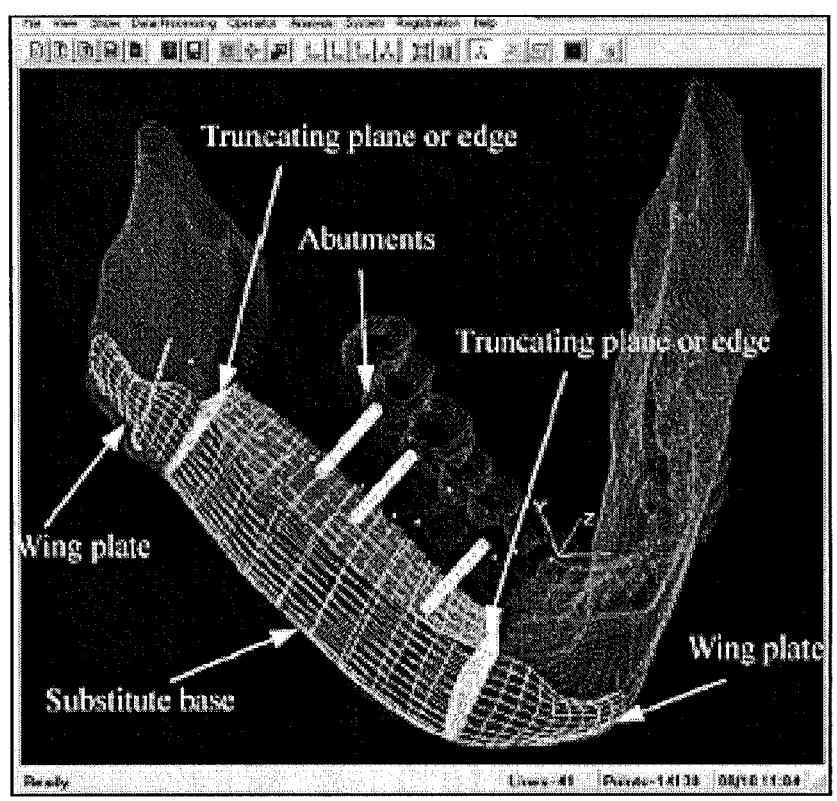
FIGS. 21A and 21B illustrate an alternate embodiment of a finished product.
Figure 21B:
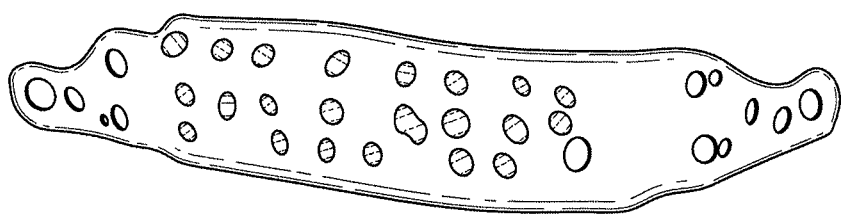
Figure 22:
FIG. 22 illustrates an alternate embodiment of a finished product.
Figure 23:
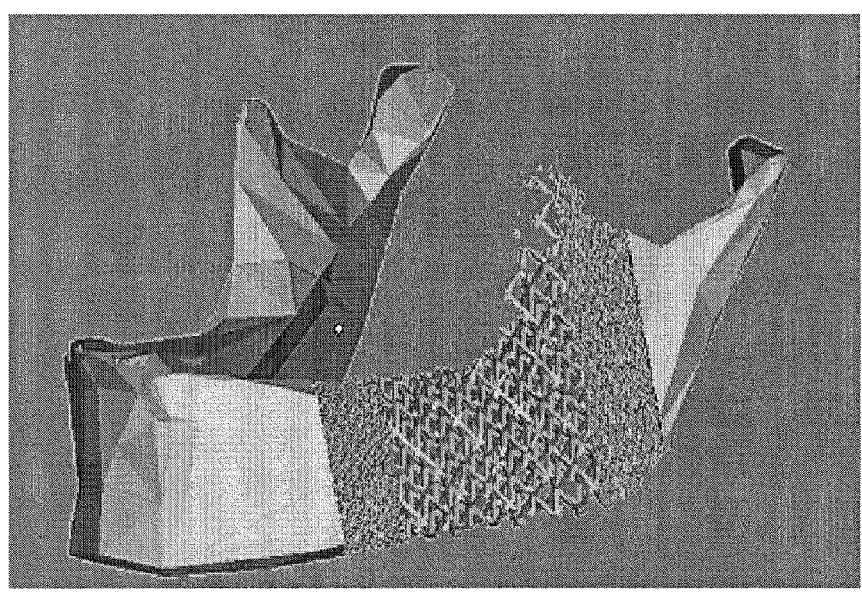
FIG. 23 illustrates an alternate embodiment of a finished product.
Figure 24A:
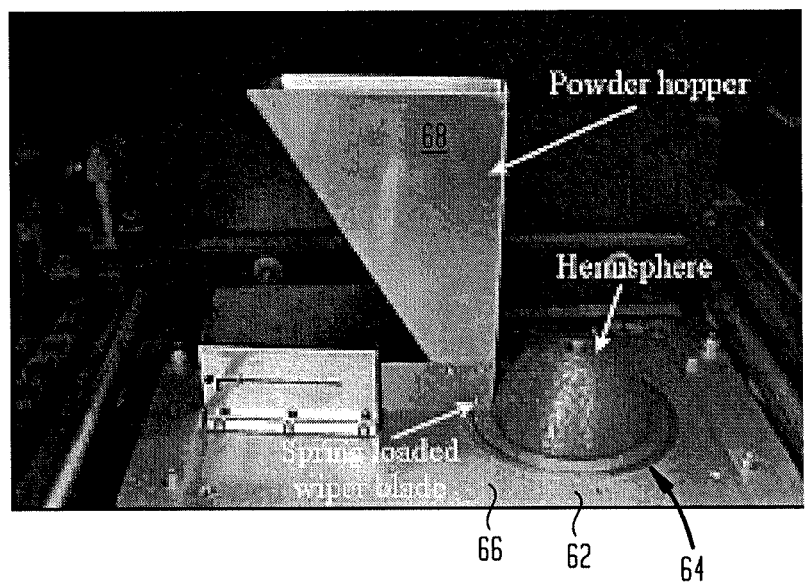
FIGS. 24A and 24B illustrate an apparatus used in conjunction with the present invention.
Figure 24B:
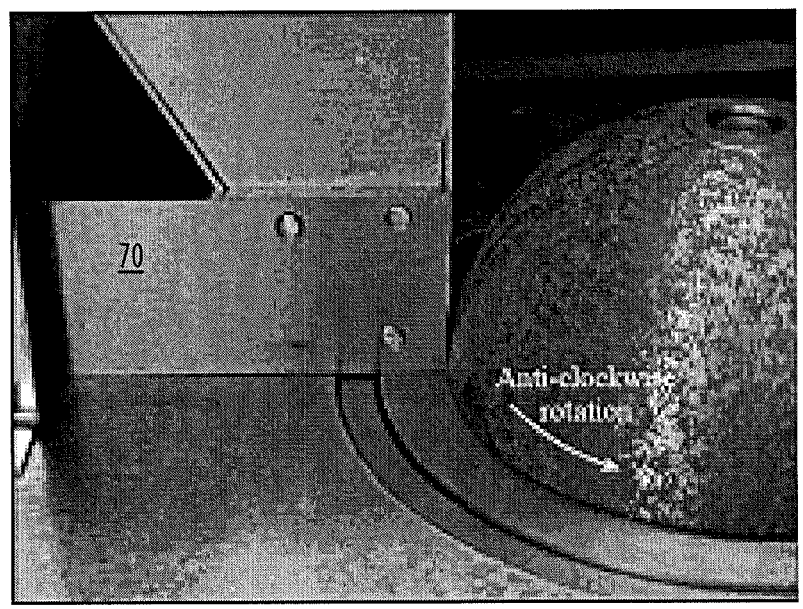
Figure 25:
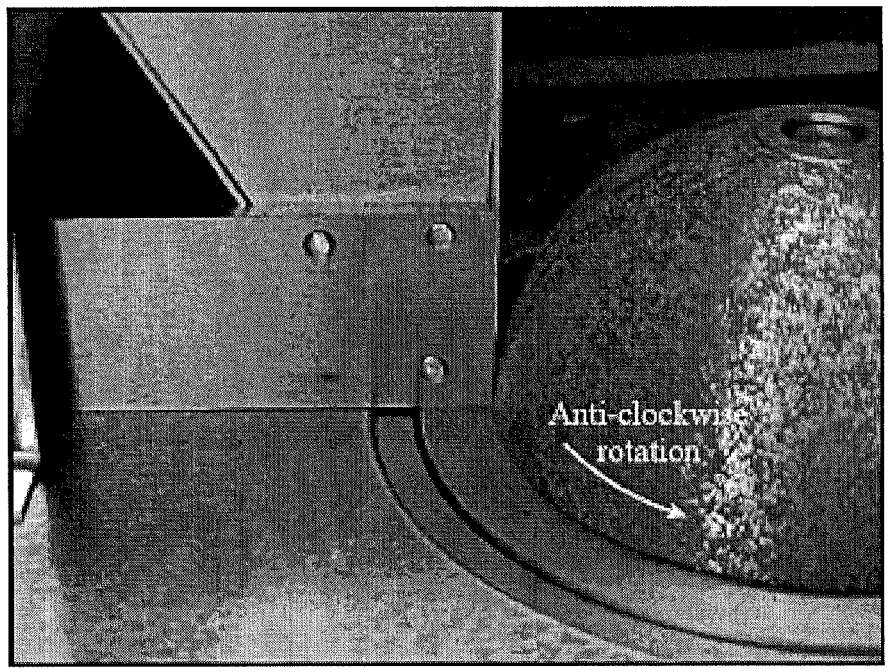
FIG. 25 illustrates a zoomed-in view of the embodiment illustrated FIG. 24B.
Figure 26:
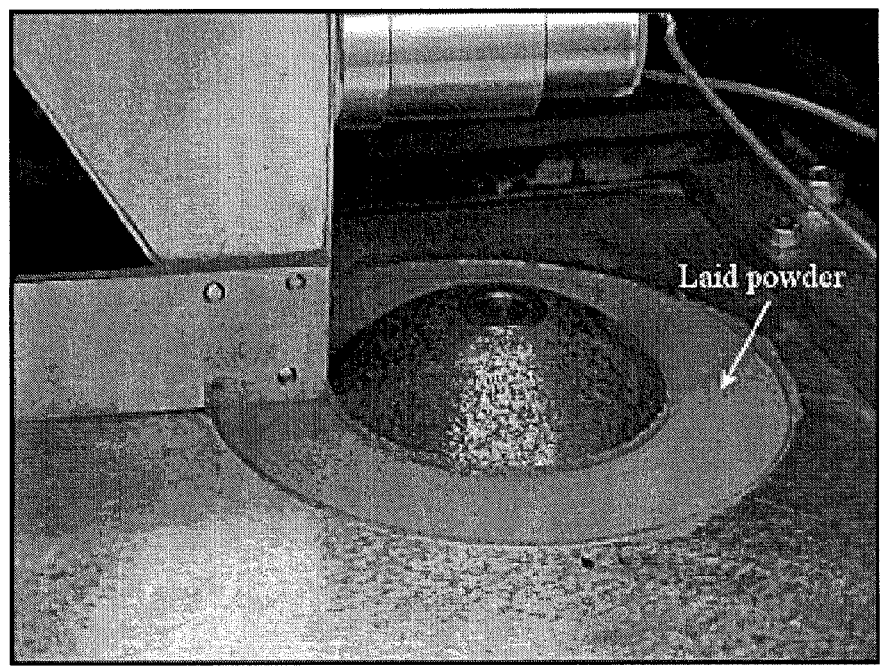
FIG. 26 illustrates a zoomed-in view of the apparatus illustrated in FIG. 24B, further along in the process.
Figure 27:
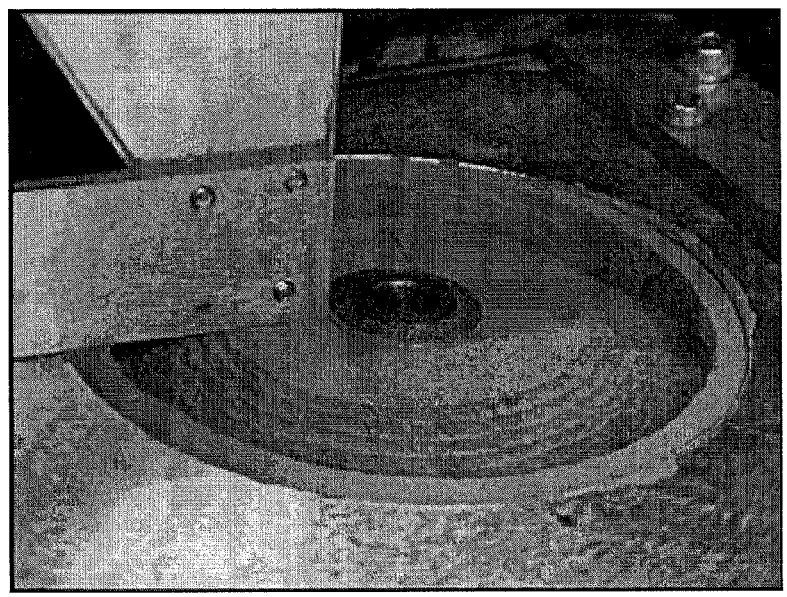
FIG. 27 illustrates a zoomed-in view of the apparatus illustrated in FIG. 24B, further along in the process.

Although the present invention has been described with regard to the femoral hip component as shown in FIG. 17, the present invention may also be used to construct additional elements. For example, other elements include an acetabular cup component illustrated in FIGS. 18A-18C, augments from knee and hip surgery, FIGS. 19A and 19B, spinal components FIGS. 20A-20C, maxillofacial reconstruction FIGS. 21A and 21B, part of a special nature, FIG. 22, and other additional irregular shapes such as that shown in FIG. 23. The list of illustrative components above is only an example of various constructs which may be composed using the method as disclosed herein and should be thought of as being inclusive as opposed to exclusive.

Figure 28A:
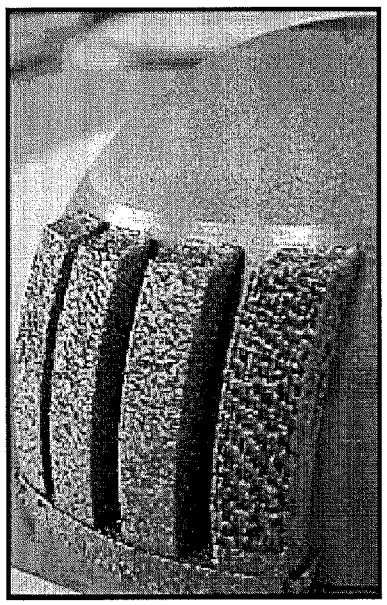
FIGS. 28A and 28B illustrate porous surface coatings being applied to a substrate.
Figure 28B:
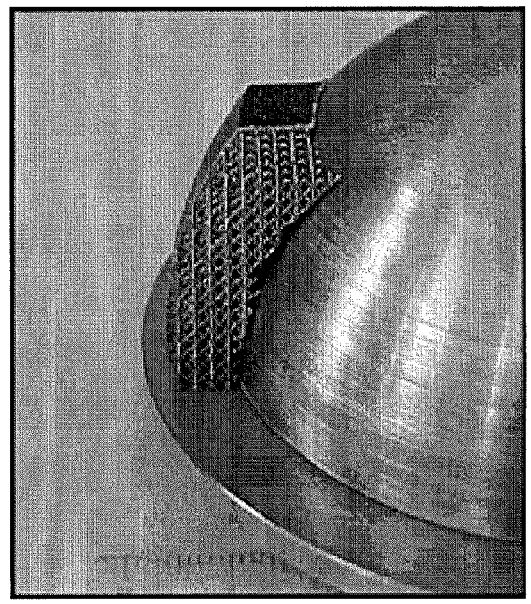
Figure 29A:
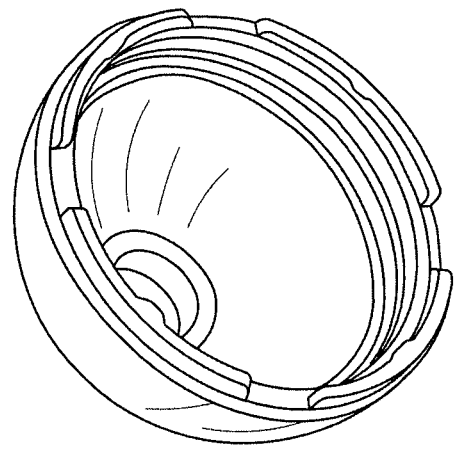
FIGS. 29A and 29B illustrate one embodiment of a representation of a finished product.
Figure 29B:
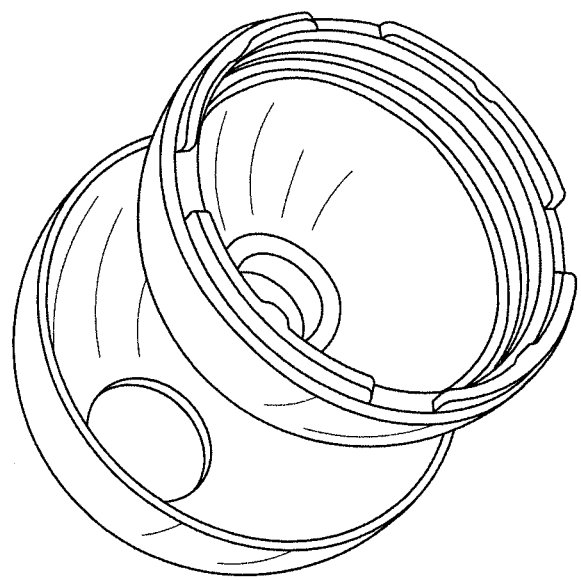
Figure 30A:
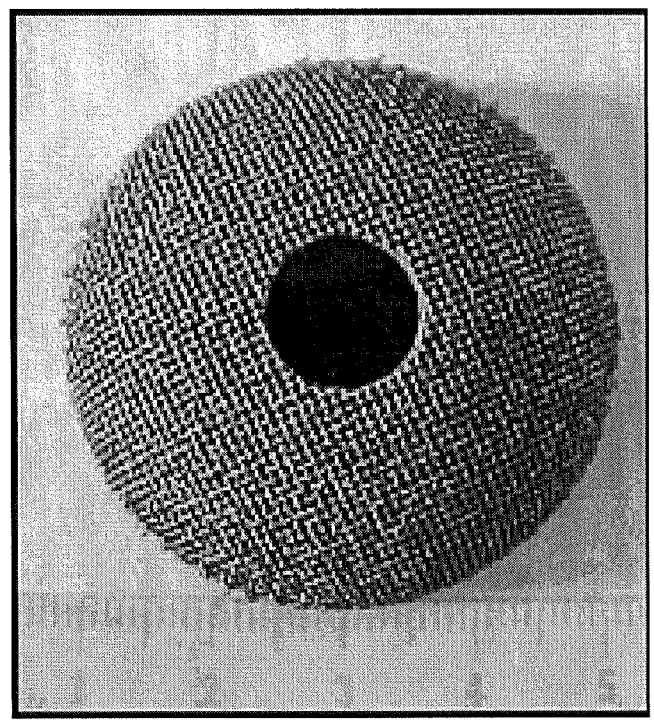
FIGS. 30A and 30B illustrate one embodiment of a finished product created using the present invention.
Figure 30B:
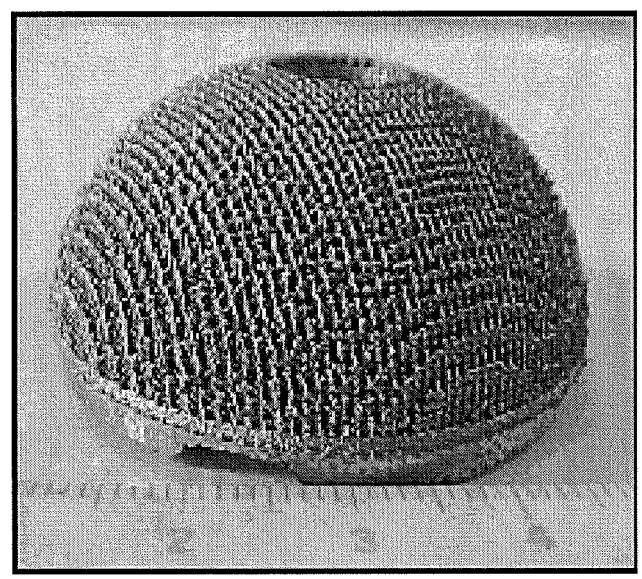

In other aspect of the present invention an existing product may be coated with various metal layers and then scanned with a laser in order to produce a finished product. In order to apply coating to existing products having either concave and/or convex profiles the present invention i.e., SLM requires the design of a special powder lay system. One such example was conducted and is shown in FIGS. 24-29. Specifically, a convex surface was created by using build apparatus 60 as shown in FIGS. 24-27. Build apparatus 60 includes a rotating piston 62 and a cylinder onto which the convex surface 64 to be coated was mounted. As the component rotates on the cylinder, it was made to drop in the Z-direction using platform 66 within the SLM machine. Powder 71 was deposited onto the side of the component using a powder hopper 68 and a wiper device 70 that runs up against the surface of the component. Once the correct amount of powder has been established a laser (not shown in the figures) in conjunction with a computer and various programming packages, including those already discussed, were used to apply a laser beam to the powder in a predetermined manner. The powder was deposited by hopper 68 and wiped to the correct height by wiper device 70. A full layer of metal powder was deposited by rotation of the cylinder through a full 360 degrees. However, the synthesis of the laser melting process and the layer production process requires that only a fraction of the circumference is layered and melted at any one time. For example, the method from production of a full layer would require that the service be built up from, possibly individual quarter revolutions and melting steps as depicted in FIG. 28. Preferably the laser melting process is fast enough that the discreet stepping process tends to be a continuous one with melting and rotation as well as layering occurring at the same time so as to increase throughput. FIGS. 24 to 27 illustrate the sequence of operations with a final coated sample being shown in FIGS. 28A and 28B. In FIG. 28A, the lattice structure was built 3 mm thick and disposed against a 70 mm diameter steel hemisphere. In FIG. 28B, the same hemisphere was used, but the lattice structure is 6 mm thick. FIG. 29 is a CAD illustration of the final assembly of a product component.

In an alternate embodiment of the present invention, the process can be parallelized by addition of many pistons and cylinder pairs around a central laser beam. Optimal laser alignment to the surface can be achieved by a number of methods, including inclining the piston and cylinder pairs so the powder surface and the part surface are correctly aligned normal to the laser beam. Typical operating parameters are shown in Table 5 below.

TABLE 5

| Slice height (µm) | Power (watts) | Exposure (µs) | $P_{dist}$ (µm) | $H_{dist}$ (mm) |
|---|---|---|---|---|
| 100 | 90.5 | 700 | 80 | 0.125 |

In another aspect of the present invention the laser produced porous structure system may be used to manufacture a porous shell which then can be inserted over a substrate and sintered in order to fix permanently to the same. Some examples include the preparation of an acetabular cup component, a tibia knee insert component, and a femoral insert as well as many additional products. In order to illustrate this aspect of the present invention, reference will be made to the outer profile of an acetabular component which serves as an inner profile of a "cap" to insure that an accurate fit is achieved when the cap is set on the substrate (acetabular shell). The cup is built to a thickness of 1.5 millimeters for example using a diamond configured construct to develop the interconnecting porosity. The metal powder used in one example is stainless steel. The processing parameters are shown in Table 6 listed below:

TABLE 6

| Slice height (µm) | Power (watts) | Exposure (µs) | $P_{dist}$ (µm) | $H_{dist}$ (mm) |
|---|---|---|---|---|
| 100 | 90.5 | 2000 | N/a | N/a |

Figure 31A:
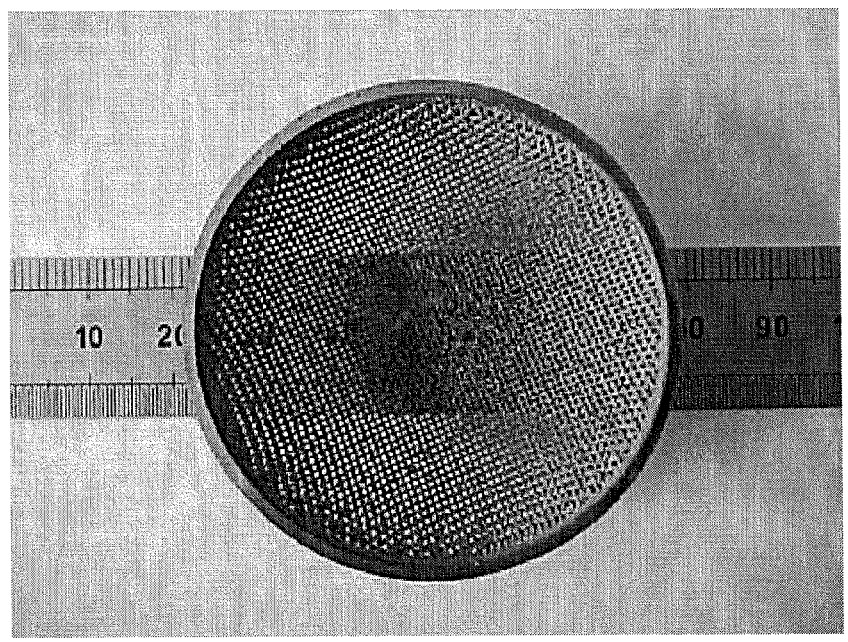
FIGS. 31A to 31D illustrate one embodiment of a finished product created using the present invention.
Figure 31B:
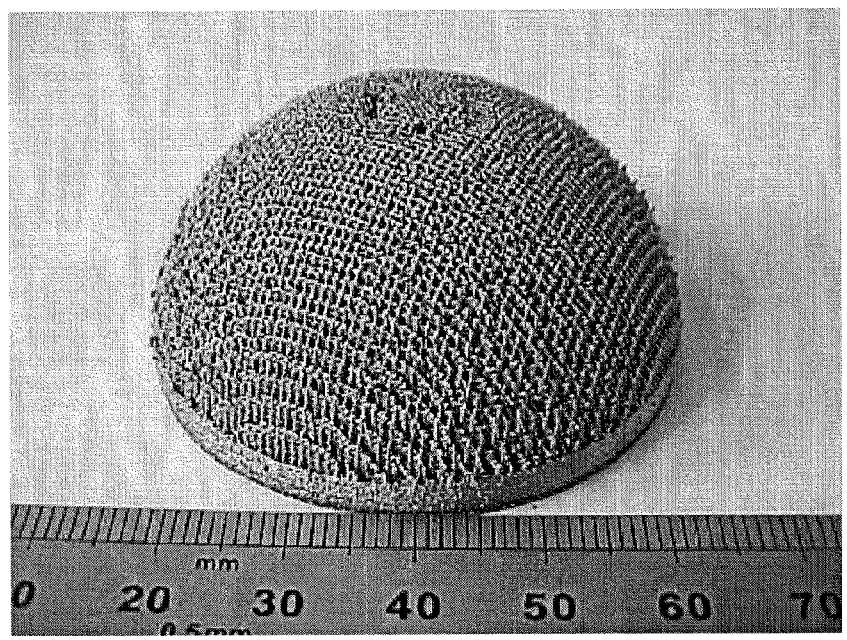
Figure 31C:
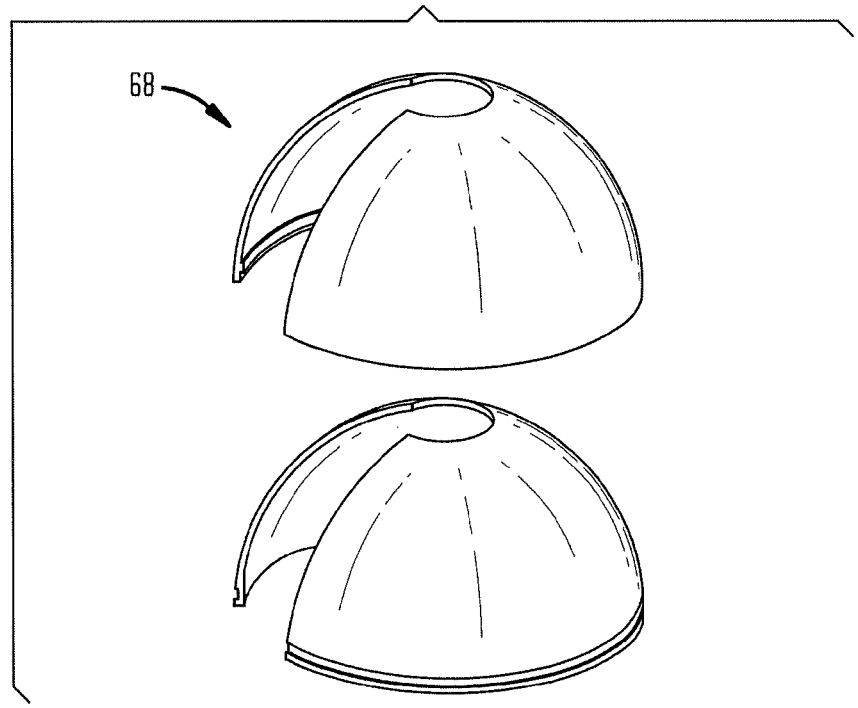
Figure 31D:
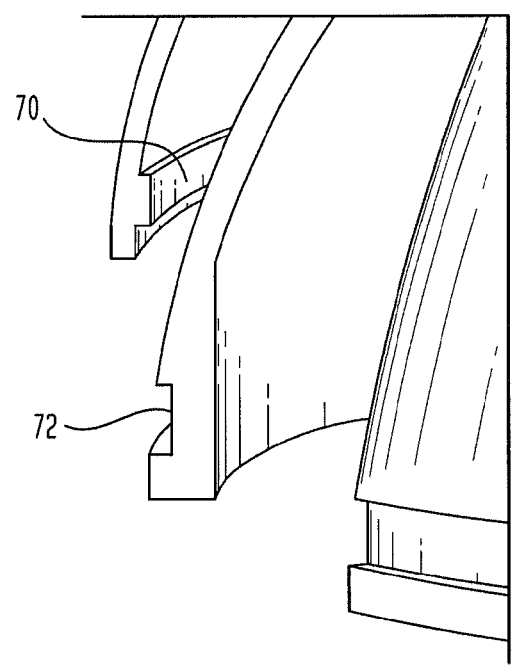

However, the process parameters are dependent on the metal used and if a different metal, say for example, titanium was used, the parameters would be different. FIG. 31A illustrates a finished product manufactured by SLM.

In order to achieve a better and tighter fit of the cap over the component, some adjustments to the geometry of the cap may be considered. For example, the inclusion of a rim 70 on the inner surface of the cap that interfaces with the groove 72 on the outer surface of the acetabular cup component 68 may be included. This mechanism acts a simple lock and gives both security and extra rigidity during the sintering process. Additional modifications may be utilized to improve closeness of the fit and stability. For instance, the introduction of "snap-fits" which are apparent in everyday plastic components may be employed to provide a more reliable attachment mechanism between the two elements. Typical pads or center pads for both the femoral and tibial knee components can be produced by the SLM process and dropped or snapped fit into place to the components and then sintered to attach firmly to the underlying substrate. As previously stated, this technique can apply to other components where a porous outer surface is required to interface with either soft or hard tissue.

A further improvement in the mechanical and microstructural properties of the porous construct may be achieved by either conventional sintering under vacuum or inert atmosphere and/or hot isostatic pressing using temperature regimes known in the state of the art. As the constructs possess high density properties throughout their strands minimal degradation in the structure of the construct is apparent.

Figure 32:
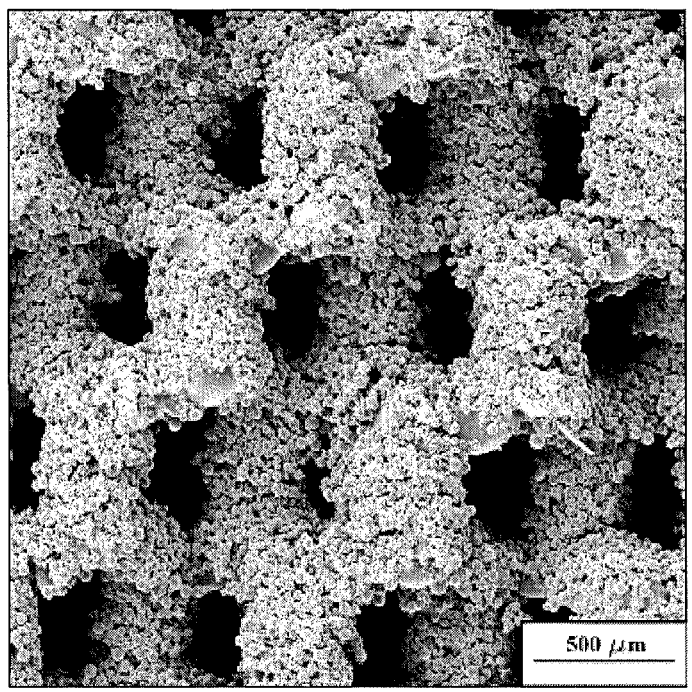
FIG. 32 illustrates a titanium lattice structure with hierarchical surface coating of sintered titanium satellites.

In another aspect of the present invention, the appearance of the porous construct can be changed by the alteration of the processing conditions or by the introduction of an acid etch process. For example, the laser power or laser residence time may be reduced or a combination of both which creates struts of the porous construct having a coating with layers of unmelted metal particles firmly adhered to the strut surfaces. This has the effect of producing additional porous features that offer a new dimension to the overall porous structure of the construct. Such features are able to interact with cells in a different manner than the microstructure imparted by the lattice construct and provide extra benefits. A typical example of such construct with this satellite appearance as depicted in FIG. 32 together with the processing parameters is employed. The structure illustrated in FIG. 32 was created using a laser power of 44.2 W and exposure time of 400 µsec. The metal layer thickness was 50 µm.

Figure 33:
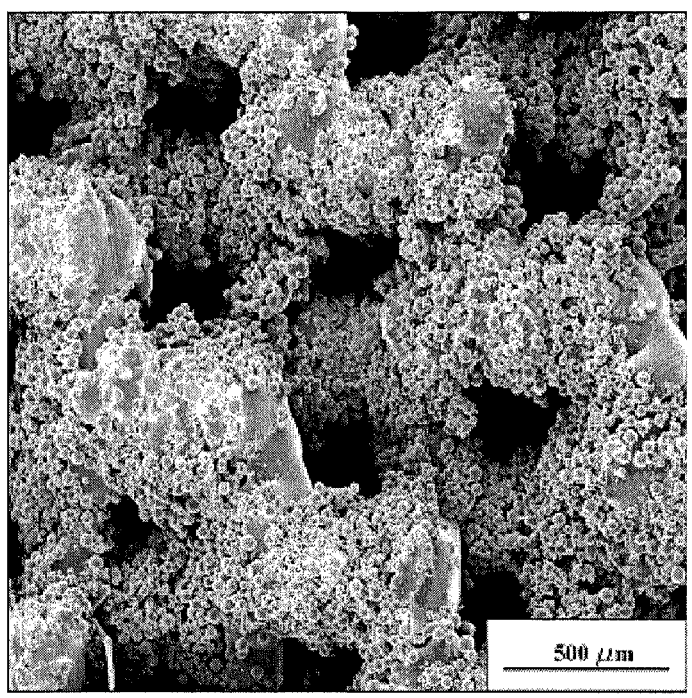
FIGS. 33-40 illustrate the change occurring to the embodiment illustrated in FIG. 32, while the lattice is exposed to a laser at increasing time periods.
Figure 34:
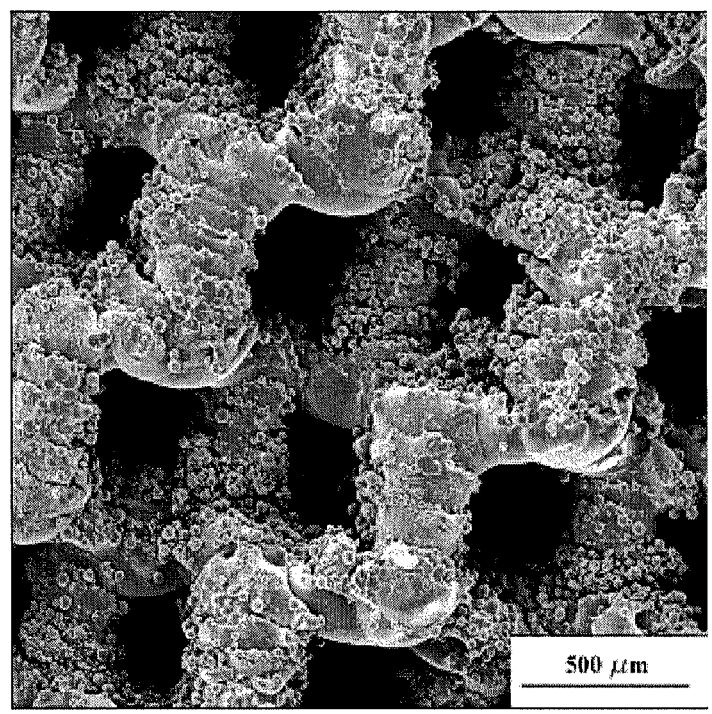
Figure 35:
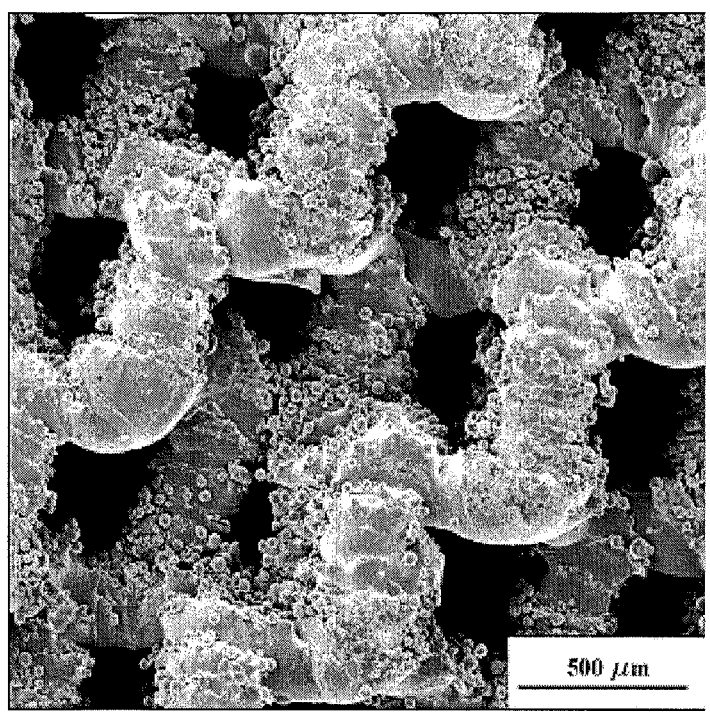
Figure 36:
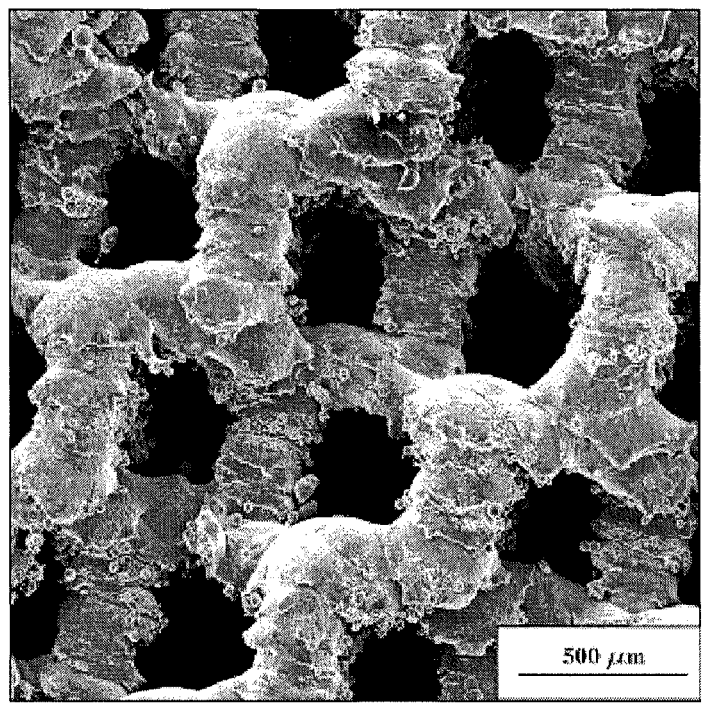
Figure 37:
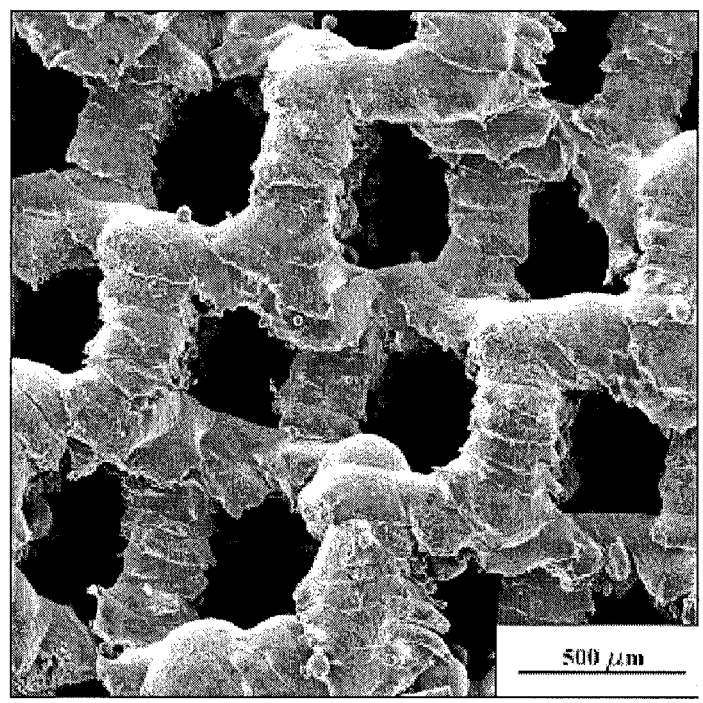
Figure 38:
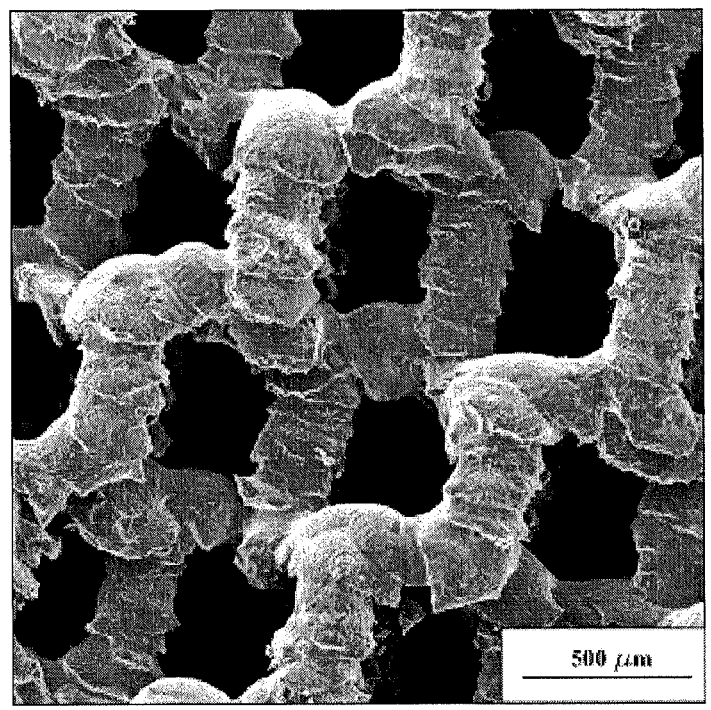
Figure 39:
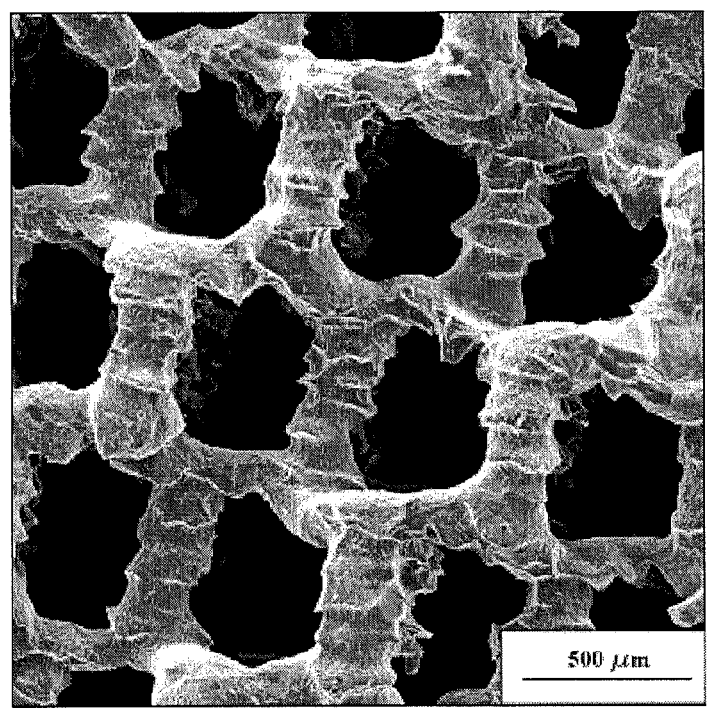
Figure 40:
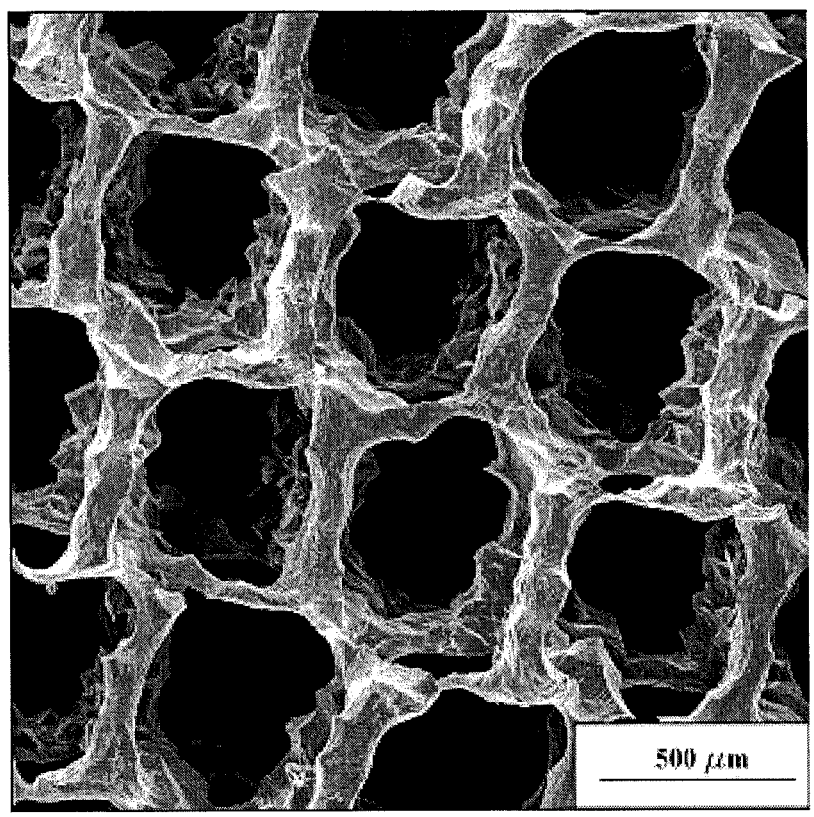

It is also possible to remove these satellites by an acid etching process and a strong acid. The acid may consist of a mixture of 10 milliliters of hydrogenfloride (HF), 5 milliliters of nitric acid ($HNO_3$) and 85 milliliters of $H_2O$. the HF and $HNO_3$ were respectively 48% and 69% concentrated. FIGS. 33 and 40 show the effects of such an acid's etch with respect to time with the relevant conditions being noted. It can be seen clearly that the solids are moved to give a pure melted lattice construct. It is also clearly evident that the overall openness within the lattice is increased by the removal of the satellites. Additionally, prolonged exposure to the acid etch mix does result in some reduction in strut thickness which may also increase the lattice size further. This enables the production of struts having a reduced thickness to be created by the STL method. Other acid types and combination may also be applied to obtain similar results.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of producing a three-dimensional porous tissue in-growth structure comprising the steps of:
    depositing a first layer of a powder made from a metal selected from the group consisting of titanium, titanium alloys, stainless steel, cobalt chrome alloys, tantalum and niobium onto a substrate;
    scanning a beam to form a plurality of points having a cross-sectional area, said points forming a portion of a plurality of predetermined unit cells within said metal powder layer;
    depositing at least one additional layer of said powder onto said first layer; and
    repeating said scanning step to form a plurality of additional points, said additional points forming additional portions of said plurality of predetermined unit cells including at least one strut having a length and a cross-sectional area, wherein said at least one strut extends in an oblique direction with respect to said substrate and said cross-sectional area along said length of said at least one strut is substantially equal to said cross-sectional area of said points.

2. The method of producing a three-dimensional porous tissue in-growth structure according to claim 1, wherein the beam has a power (P) for a period of time (μsec) with a point distance (μm).

3. The method of producing a three-dimensional porous tissue in-growth structure according to claim 2, wherein the beam is an electron beam.

4. The method of producing a three-dimensional porous tissue in-growth structure according to claim 2, wherein the beam is a laser beam.

5. The method of producing a three-dimensional porous tissue in-growth structure according to claim 4, wherein said laser power is 90.5 W, said exposure time is 1000 μsec and said point distance is 90 μm.

6. The method of producing a three-dimensional porous tissue in-growth structure according to claim 1, wherein at least some of said predetermined unit cells are a tetrahedron.

7. The method of producing a three-dimensional porous tissue in-growth structure according to claim 1, wherein at least some of said predetermined unit cells are a dodecahedron.

8. The method of producing a three-dimensional porous tissue in-growth structure according to claim 1, wherein at least some of said predetermined unit cells are an octahedron.

9. The method of producing a three-dimensional porous tissue in-growth structure according to claim 1, wherein at least some of said predetermined unit cells are truncated.

10. The method of producing a three-dimensional porous tissue in-growth structure according to claim 1, wherein said first layer of metal powder has a thickness between 5 μm to 2000 μm.

11. The method of producing a three-dimensional porous tissue in-growth structure according to claim 1, wherein said at least one additional layer of powder has a thickness between 5 μm to 2000 μm.

12. The method of producing a three-dimensional porous tissue in-growth structure according to claim 1, further comprising predetermining a porosity range for at least one deposited powder layer and scanning said at least one deposited powder layer in a manner to provide said deposited powder layer with a porosity within said porosity range.

13. The method of producing a three-dimensional porous tissue in-growth structure according to claim 1, wherein said substrate is a base or core made of a metal selected from the group consisting of titanium, titanium alloys, stainless steel, cobalt chrome alloys, tantalum and niobium, wherein said first layer is fused to said base or core.

14. The method of producing a three-dimensional porous tissue in-growth structure according to claim 13, further comprising sintering at least a portion of said first powder layer to said base or core.

15. The method of producing a three-dimensional porous tissue in-growth structure according to claim 13, wherein said base or core is separated from said first layer.

16. The method of producing a three-dimensional porous tissue in-growth structure according to claim 15, wherein said base or core is integral with said first layer and imparts additional physical properties to an overall construct.

17. The method of producing a three-dimensional porous tissue in-growth structure according to claim 1, wherein a solid or a semi-pervious layer is placed between said substrate and said first metal powder layer.

18. The method of producing a three-dimensional porous tissue in-growth structure according to claim 1, wherein during the step of scanning said powder layer a plurality of satellites are formed on portions of said predetermined unit cells.

19. The method of producing a three-dimensional porous tissue in-growth structure according to claim 18, further comprising an acid etching process to remove said satellites.

20. The method of producing a three-dimensional porous tissue in-growth structure according to claim 1, wherein at least some of said predetermined unit cells are truncated to provide a barb effect.

21. A method of producing a three-dimensional porous tissue in-growth structure comprising the steps of:
depositing a first layer of a powder made from a metal selected from the group consisting of titanium, titanium alloys, stainless steel, cobalt chrome alloys, tantalum and niobium onto a substrate;
scanning a beam to form a portion of a plurality of predetermined unit cells within said metal powder layer;
depositing at least one additional layer of said powder onto said first layer; and
repeating said scanning step to form additional portions of said plurality of predetermined unit cells, said portions forming at least one strut having a length and a cross-sectional area, wherein the at least one strut extends in an oblique direction with respect to said substrate and said cross-sectional area of said at least one strut is substantially equal along said length of said at least one strut.

* * * * *